(12) United States Patent
Adamo et al.

(10) Patent No.: US 8,304,532 B2
(45) Date of Patent: Nov. 6, 2012

(54) METHOD FOR PREPARING OLIGONUCLEOTIDES

(75) Inventors: Ilaria Adamo, Fagagna (IT); Cecile Dueymes, Rodez (FR); Andreas Schonberger, Muden/Aller (DE); Jean-Louis Imbach, Montpellier (FR); Albert Meyer, Perols (FR); Francois Morvan, Castelnau le Lez (FR); Francoise Debart, Combaillaux (FR); Jean-Jacques Vasseur, Combaillaux (FR); Meinolf Lange, Halle/Westf. (DE); Fritz Link, Bergisch-Gladbach (DE)

(73) Assignees: Girindus AG, Bergisch-Gladbach (DE); Centre National de la Recherche Scientifique, Paris Cedex (FR); University of Montpellier II, Montpellier Cedex (FR)

( * ) Notice: Subject to any disclaimer, the term of this patent is extended or adjusted under 35 U.S.C. 154(b) by 0 days.

(21) Appl. No.: 13/115,845

(22) Filed: May 25, 2011

(65) Prior Publication Data

US 2011/0224424 A1 Sep. 15, 2011

Related U.S. Application Data

(63) Continuation of application No. 12/417,750, filed on Apr. 3, 2009, now abandoned, which is a continuation of application No. 10/522,854, filed as application No. PCT/EP03/08447 on Jul. 30, 2003, now abandoned.

(60) Provisional application No. 60/399,412, filed on Jul. 31, 2002.

(30) Foreign Application Priority Data

Jul. 31, 2002 (EP) ..................................... 02017211

(51) Int. Cl.
*C07H 21/00* (2006.01)
(52) U.S. Cl. .................................................. 536/25.34
(58) Field of Classification Search .................. None
See application file for complete search history.

(56) References Cited

U.S. PATENT DOCUMENTS

| | | | | |
|---|---|---|---|---|
| 3,338,883 A | * | 8/1967 | Tesoro et al. | 536/30 |
| 3,506,676 A | * | 4/1970 | Tesoro et al. | 546/267 |
| 3,682,997 A | * | 8/1972 | Tesoro et al. | 560/308 |
| 4,415,732 A | * | 11/1983 | Caruthers et al. | 536/26.5 |
| 4,458,066 A | * | 7/1984 | Caruthers et al. | 536/25.34 |
| 4,500,707 A | * | 2/1985 | Caruthers et al. | 536/25.34 |
| 4,668,777 A | * | 5/1987 | Caruthers et al. | 536/26.5 |
| 4,973,679 A | * | 11/1990 | Caruthers et al. | 536/26.71 |
| 5,132,418 A | * | 7/1992 | Caruthers et al. | 536/25.3 |
| 5,194,599 A | * | 3/1993 | Froehler et al. | 536/26.72 |
| 5,565,555 A | * | 10/1996 | Froehler et al. | 536/26.22 |
| 5,574,146 A | | 11/1996 | Reddy et al. | |
| 5,808,042 A | | 9/1998 | Iyer et al. | |
| 6,300,486 B1 | * | 10/2001 | Froehler et al. | 536/23.1 |
| 6,306,599 B1 | | 10/2001 | Perbost | |
| 6,756,496 B1 | * | 6/2004 | Froehler et al. | 536/26.6 |
| 2004/0265870 A1 | | 12/2004 | Lee et al. | |

FOREIGN PATENT DOCUMENTS

| | | |
|---|---|---|
| WO | WO 99/52926 A1 | 10/1999 |
| WO | WO99/62922 A1 * | 12/1999 |
| WO | WO 01/51532 A1 | 7/2001 |
| WO | WO 01/64702 A1 | 9/2001 |
| WO | WO2004/013154 A1 * | 2/2004 |

OTHER PUBLICATIONS

Caruthers (I), "DNA Synthesis for Nonchemists: The Phosphoramidite Method on Silica Supports," Chapter 3 in Synthesis and Applications of DNA and RNA, Narang, S.A. (ed.), Academic Press, Inc., New York, NY, 1987, only pp. 47-94 supplied.*
Zon & Stec, "Phosphorothioate Oligonucleotides," Chapter 4 in Oligonucleotides and Analogues, A Practical Approach, Eckstein, F. (ed.), IRL Press, Inc., New York, NY, 1991, only pp. 87-108 supplied.*
Caruthers (II), "Synthesis of Oligonucleotides and Oligonucleotide Analogues," Chapter 1 in Oligonucleotides—Antisense Inhibitors of Gene Expression, Cohen, J. S. (ed.), CRC Press, Inc., Boca Raton, Florida, 1989, only pp. 7-24 supplied.*
Stein & Cohen, "Phosphorothioate Oligonucleotide Analogues," Chapter 5 in Oligonucleotides—Antisense Inhibitors of Gene Expression, Cohen, J. S. (ed.), CRC Press, Inc., Boca Raton, Florida, 1989, only pp. 97-117 supplied.*

(Continued)

*Primary Examiner* — Lawrence E Crane
(74) *Attorney, Agent, or Firm* — Mayer Brown LLP

(57) ABSTRACT

A solution phase synthesis method for preparing an oligonucleotide, wherein at least some of the reagents are solid supported. The method suitable for large-scale synthesis comprises coupling a protected compound with a nucleotide derivative having a protection group in the presence of a solid supported activator to give an elongated oligonucleotide with a P(III)-internucleotide bond; optionally processing the elongated oligonucleotide by capping by reaction with a solid supported capping agent and/or by oxidizing or sulfurizing by reaction of the oligonucleotide with a solid supported oxidizing or sulfurization reagent; and removing the protection group. The coupling may include reacting a 3'-protected compound of formula:

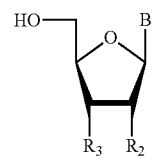

with a nucleotide derivative having a 5'-protection group, or reacting a 5'-protected compound of formula

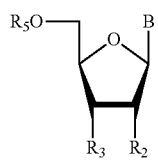

with a nucleotide derivative having a 3'-protection group.

20 Claims, No Drawings

OTHER PUBLICATIONS

Patil et al., "A Facile Method for Detritylation of 5'-O-dimethoxytrityl-3'-O-tert-butyldimethylsilyl-2-deoxynucleosides," *Synthetic Communications*, 24(7), 2423-2428 (1994).*

Morvan et al., "Solid-Phase Synthesis of Di- and Tri-Nucleotides Using Polymer Supported Reagents," pp. 1-15 of Unit 3.14 in Supplement 26 of Current Protocols in Nucleic Acid Chemistry, John Wiley & Sons, Inc., New York, NY, 2006.*

Efimov et al., "New Efficient Sulfurizing Reagents for the Preparation of Oligodeoxyribonucleotide Phosphorothioate Analogs," *Nucleic Acids Research*, 240, 4029-4033 (1995).*

Dueymes et al., "High-Yield Solution-Based Synthesis of Di- and Trinucleotide Blocks Assisted by Polymer Supported Reagents," *Organic Letters*, 7(16), 3485-3488 (Jul. 12, 2005).*

Beaucage, S.L. and Caruthers, M.H., "Synthetic Strategies and Parameters Involved in the Synthesis of Oligodeoxyribonuclecotides According to the Phosphoramidite Method," in *Current Protocols in Nucleic Acid Chemistry*, Beaucage, S.L., et al., eds., John Wiley & Sons, Inc., pp. 3.3.1-3.3.20 (2000).

Beaucage, S.L. and Iyer, R.P., "Tetrahedron Report No. 309," *Tetrahedron* 48:2223-2311, Pergamon Press Ltd. (1992).

Dabkowski, W., et al., "2,4-Dinitrophenol: a novel activating reagent in nucleotide synthesis via the phosphoramidite route. Design of new effective phosphitylating reagents," *Tet. Lett.* 41:7535-7539, Elsevier Science Ltd. (2000).

Froehler, B.C., "Oligodeoxynucleotide Synthesis: *H-Phosphonate Approach*," in *Methods in Molecular Biology*, Agrawal, S., ed., Humana Press Inc., Totowa, NJ, Chapter 4, pp. 63-80 (1993).

International Search Report for International Application No. PCT/EP2003/08447, European Patent Office, mailed Nov. 3, 2003.

Reese, C.B. and Song, Q., "The *H*-phosphonate approach to the solution phase synthesis of linear and cyclic oligoribonucleotides," *Nucleic Acid Res.* 27:963-971, Oxford University Press (1999).

Strömberg, R. and Stawinski, J., "Synthesis of Oligodeoxyribo- and Oligoribonucleotides According to the *H*-Phophonate Method," in *Current Protocols in Nucleic Acid Chemistry*, Beaucage, S.L., et al., eds., John Wiley & Sons, Inc., pp. 3.4.1-3.4.15 (Dec. 2004).

Takeshita, M., et al., "Oligodeoxynucleotides Containing Synthetic Abasic Sites," *J. Biol. Chem.* 262:10171-10179, The American Society of Biological Chemists, Inc. (1987).

Vinš, I. and Kábrt, L., "Ion Chromatographic Separation and Determination of Some Sulphur Anions," *Coll. Czech. Chem. Commun.* 52:1167-1171, Institute of Organic Chemistry and Biochemistry (1987).

Vláčil, F. and Vinš, I., "Modified Hydroxyethyl Methacrylate Copolymers As Sorbents for Ion Chromatography," *J. Chromat.* 391:119-132, Elsevier Science Publishers B.V. (1987).

* cited by examiner

METHOD FOR PREPARING OLIGONUCLEOTIDES

CROSS-REFERENCE TO RELATED APPLICATIONS

This application is a continuation application of U.S. Utility application Ser. No. 12/417,750, filed on Apr. 3, 2009 now abandoned, which is a continuation application of U.S. Utility application Ser. No. 10/522,854, filed on Nov. 8, 2005 now abandoned, which is a U.S. national stage application under 35 U.S.C. §371 of International Application No. PCT/EP2003/008447 filed on Jul. 30, 2003, which claims priority to European Application No. 02017211.0 filed on Jul. 31, 2002 and to U.S. Provisional Application No. 60/399,412, filed on Jul. 31, 2002, these applications being herein incorporated by reference in their entirety for all purposes.

The present invention relates to a method for preparing oligonucleotides.

The synthesis of oligonucleotides has been the subject of investigations for a long period of time. Automated synthesis procedures have been developed and apparatus for the automated syntheses are commercially available. Most of these procedures have been developed for rather small quantities of oligonucleotides (in the range of mg). These amounts are sufficient for most investigational purposes.

Especially with the development of antisense therapeutics, large scale synthesis became a matter of considerable importance. Although relative large scale amounts of oligonucleotides have been obtained by scale-up of solid phase synthesis procedures, these technologies show major limitations especially high costs for reagents and materials, e.g. the solid phase bound starting oligonucleotide.

With scale-up, the reaction time of each step of the synthesis increases.

Furthermore oligonucleotides synthesis by standard solid phase synthesis results in a contamination of the desired full length compound by failure sequences arising from incomplete reaction during the synthesis cycle. At large scales the purification of the crude oligonucleotide involves complicated isolation and chromatographic purification of the final product.

In general, synthesis methods for oligonucleotides consist of a four-step procedure for the elongation of the oligonucleotide 1. Coupling
2. Capping
3. Oxidation
4. Deprotection of the protected hydroxyl group for the next reaction cycle.

One object of the present invention is to provide a method for the preparation of oligonucleotides suitable for large scale (kilogram to tons) synthesis.

A further object of the present invention is to provide a method for the preparation of oligonucleotides avoiding complicated purification steps, especially chromatographic purifications, especially during synthesis cycles.

A further object of the invention is to provide a method for the preparation of oligonucleotides allowing an effective convergent synthesis.

In one embodiment this object is solved by a liquid phase synthesis method, comprising the steps of
a) providing a 3'-protected compound having the formula;

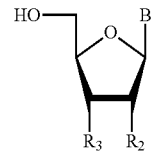

wherein
B is a heterocyclic base
$R_2$ is H, a protected 2'-hydroxyl group, F, a protected amino group, an O-alkyl group, an O-substituted alkyl, a substituted alkylamino or a C4'-O2'methylen linkage
$R_3$ is $OR'_3$, $NHR''_3$, $NR'_3R'''_3$, a 3'-protected nucleotide or a 3'-protected oligonucleotide,
$R'_3$ is a hydroxyl protecting group,
$R''_3$, $R'''_3$ are independently an amine protecting group,
b) reacting said compound with a nucleotide derivative having a 5'-proctection group in the presence of a solid supported activator to give an elongated oligonucleotide with a P(III)-internucleotide bond
c) optionally processing the elongated oligonucleotide with a P(III)-internucleotide bond by either or both of steps c1) and c2) in any sequence
   c1) capping, preferably by reacting with a solid supported capping agent
   c2) oxidizing, preferably by reacting the oligonucleotide with a solid supported oxidizing reagent
d) removing the 5'-protection group.

The method of the present invention is a solution phase synthesis wherein at least some of the reagents are solid supported. "Solid supported" covers covelently bound reagents and reagents bound to a solid support by ionic forces.

In a preferred embodiment, step d) is effected by treatment with a solid supported agent or removing the 5'-protection group with a removal agent followed by addition of a solid supported scavenger or followed by extraction.

In most cases coupling occurs of a 5'-OH-synthon with a 3'-phosphorous-synthon. Alternatively coupling of a 5'-phosphorous-synthon with a 3'-OH-synthon is also possible. Therefore in a further embodiment the invention comprises a method comprising the steps of
a) providing a 5'-protected compound having the formula:

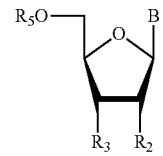

wherein
B is a heterocyclic base
$R_2$ is H, a protected 2'-hydroxyl group, F, a protected amino group, an O-alkyl group, an O-substituted alkyl, a substituted alkylamino or a C4'-O2'methylen linkage
$R_3$ is OH, $NH_2$
$R_5$ is a hydroxyl protecting group, a 5'-protected nucleotide or a 5'-protected oligonucleotide
b) reacting said compound with a nucleotide derivative having a 3'-proctection group in the presence of a solid supported activator to give an elongated oilgonucleotide with a P(III)-internucleotide bond
c) optionally processing the elongated oligonucleotide with a internucleotide bond by either or both of steps c1) and c2) in any sequence
   c1) capping, preferably by reacting with a solid supported capping agent
   c2) oxidizing, preferably by reacting the oligonucleotide with a solid supported oxidizing reagent
d) removing the 3'-protection group.

In a preferred embodiment, step d) is effected by treatment with a solid sup-ported agent or removing the 3'-protection group with a removal agent followed by addition of a solid supported scaenger or followed by extraction.

In further embodiments, it is possible to couple a 3'-phosphorous synthon with a 3'-OH synthon to form a non-natural 3'-3'-internucleosidic linkage. For the synthesis of non-natural 5'-5'-internucleosidic linkages it is possible to react a 5'-phosphorous synthon with a 5'-OH synthon. These non-natural internucleosidic linkages show increased nuclease resistance.

Step a)

B, the heterocyclic base can be a natural nucleobase or a modified one including a non-base residue. The natural nucleobasis are adenine, guanine, thymine, cytosine and uracil. In general these bases need protection groups during the synthesis. Suitable protected nucleobases are known to persons skilled in the art for example N-4-benzoylcytosine, N-6-benzoyl adenine, N-2-isobutiryl guanine, N-4-acetyl or isobutyril cytosine, N-6-phenoxyacetyl adenine, N-2-tert-butyl phenoxyacetyl guanine. Suitable non-base residues include for example Hydrogen, H leading to the 1',2'-dideoxyribose (dSpacer from Glen Research) which can be used as linker or to mimic abasic sites in an oligonucleotide (Takeshita et al., J. Biol. Chem, 1987, 262, 10171).

Furthermore, it is also possible to use isomers of nucleosides such as L, D, α, β and the like.

A suitable protection for the 2'-hydroxyl-group include but are not limited to tert-butyl dimethylsilyl (TBDMS), triisopropyisilyloxymethyl (TOM), fluorophenyl-metoxypiperidinyl (FPMP).

Suitable protecting groups for the 3'-hydroxyl-group include but are not limited to tert-butyl dimethylsilyl (TBDMS), levulinyl, benzoyle. This compound is then reacted with a nucleotide derivative with a 3'-phosphorous-synthon. The nucleotide derivative preferably has the following formula

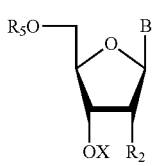

(Formula III)

wherein
X is a P(III)-function
B is a heterocyclic base
$R_2$ is H, a protected 2'-hydroxyl group, F, a protected amino group, an O-alkyl group, an O-substituted alkyl, a substituted alkylamino or a C4'-O2'methylen linkage
$R_5$ is a hydroxyl protecting group, a 5'-protected nucleotide or a 5'-protected oligonucleotide.

In the second embodiment, the nucleotide derivative preferably has the following formula

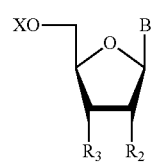

(Formula IV)

wherein
X is a P(III)-function
B is a heterocyclic base
$R_2$ is H, a protected 2'-hydroxyl group, F, a protected amino group, an O-alkyl group, an O-substituted alkyl, a substituted alkylamino or a C4'-O2'methylen linkage
$R_3 = OR'_3$, $NHR''_3$, $NR''_3R'''_3$, a 3'-protected nucleotide or a 3'-protected oligonucleotide,
$R'_3$ is a hydroxyl protecting group,
$R''_3$, $R'''_3$ are independently an amine protecting group,
$R'_3$ is a hydroxyl protecting group, a 3'-protected nucleotide or a 3'-protected oligonucleotide Step b): The Coupling Step In step b) the coupling of the nucleotide or oligonucleotides occurs. The chemistry of the reaction depends on the type of activated phosphorous compound.

Several methods for coupling nucleotides are known. The most common methods are via phosphoramidite and via H-phosphonate. In each of these cases the phosphor is in an activated state which allows coupling with the free hydroxyl group of the other part.

In phosphoramidite chemistry (Beaucage et al., Tetrahedron, 1992, 48, 2223-2311: Beaucage and Caruthers in unit 3.3 of Current Protocols in Nucleic Acid Chemistry, Wiley) a nucleoside or oligonucleotide-3'-O-phosphoramidite where the P(III) phosphorus is substituted with a dialkylamine (phosphite activating group) and a phosphorus protecting group (including but not limited to 2-cyanoethyl, methyl) is reacted with 5'-hydroxyl nucleoside or oligonucleotide in presence of an activator to create a phosphite triester internucleosidic linkage.

In H-phosphonate chemistry (Froehler, Methods in Molecular Biology. Protocols for oligonucleotides and analogs, Humana Press, 1993, 63-80; Strömberg and Stawinski, in unit 3.4 of Current Protocols in Nucleic Acid Chemistry, Wiley) a nucleoside or oligonucleotide-3'-O—H-phosphonate is reacted with a 5'-hydroxyl nucleoside or oligonucleotide in presence of an activator to create a H-phosphonate diester internucleosidic linkage.

Suitable activators for the coupling step in phosphoramidite chemistry include, but are not limited to a solid support bearing a pyridinium salt, for example a solid support covalently linked to pyridine e.g. poly(vinyl)-pyridinlum or the pyridinium is a counter ion of a cation exchange solid support. The cation exchange support can be a strong or a weak exchanger, for example a sulfonic acid or a carboxylic acid. The pyridinium salt can also be a substituted pyridinium salt, for example dichloropyridinium. It can further be a solid support bearing an optionally substituted azole (imidazole, triazole, tetrazole), or is the salt of a weak base anion exchange resin with a strong acid, or a weak cation exchange resin (carboxylic) in its protonated form (see U.S. Pat. No. 5,574,146), or a solid support bearing an optionally substituted phenol (see W. Dabkowski and al., Tet Lett, 2000, 41, 7535-7539).

The use of imidazole is less preferred.

For the H-phosphonate method the suitable activators include, but are not limited to solid supports bearing a carboxylic acid chloride, sulfonic acid chloride, a chloroformate, a chlorosulfite or a phosphorochloridate or the respective Br-compounds. Further compounds are disclosed in WO 01/64702A1, page 6, line 36 to page 8, line 5, incorporated by reference and C B Reese and Q Song, Nucleic Acid Res., 1999, 27, 963-971.

Step c) Capping and Oxidizing

Capping is understood as a reaction wherein a reagent reacts with remaining protected compounds of step a). As the capping agent is preferably solid supported, the 3'-protected compound can be removed together with the solid supported capping agent.

For the capping step suitable reagents suitable capping agents include, but are not limited to activated acids for example carboxylic acid, chloride or sulfonic acid chloride, carboxylic acid bromide, azolide, substituted azolide, anhydride or chloroformate or phosphorochloridate, or a solid supported phosphoramidate, or a solid supported H-phosphonate monoester. The acid group is preferably an acid group covalently bound to a solid support. Commercially available cationic exchanger resins can be used as a starting material for synthesizing the solid supported carboxylic acids or sulfonic acids.

The oxidizing reaction is used to oxidize the P(III)-internucleotide bond to a P(V)-internucleotide bond, Capping can be performed before oxidizing and vice versa. Depending on the reagents capping and oxidizing may also be combined in one step.

In case of H-phosphonate chemistry, the oxidizing step is preferably done in every second or third cycle or at the end of synthesis only. In phosphoamidite chemistry removal of the excess of 5' nucleoside oligonucleotide can be facsilated by a hydrolysis step, for example with water.

For the oxidizing step the oxidizing reagent can be any oxidizing reagent used for prior art solid phases, preferably in the form of solid supported agent, either covalently bound or bound by ionic forces. Suitable reagents are solid supported periodates, permanganates, osmium tetroxides, dichromates, hydroperoxides, substituted alkylamine oxides, percarboxylic acid and persulfonic acid.

These compounds are negatively charged, therefore they can be solid supported by a suitable Ion exchanger for example an ion exchanger bearing ammonium groups. These substances could be bound to solid support consisting for example of an amino, alkyl amino, dialkyl amino or trialkyl amino anion exchanger.

In oligonucleotides synthesis for investigational purposes and especially for antisense therapeutics phosphorthioate analogs are used. In this case the oxidizing is a sulfurization. As a solid supported oxidizing reagent a solid supported sulfurization reagent is used, for example a solid supported tetrathionate, a solid supported alkyl or aryl sulfonyl disulfide, a solid supported optionally substituted dibenzoyl tetrasulfide, a solid supported bis(akyloxythlocarbonyptetrasuifide, a solid supported optionally substituted phenylacetyl disulfide, a solid supported N-[(alkyl or aryl)sulfanyl]alkyl or aryl substituted succinimide and a solid supported (2-pyridinyidithio) alkyl or aryl.

Very preferred is a solid supported cyanoethylthiosulfate ($NC-CH_2-CH_2S-SO_3^-$), available according to the procedure in U.S. Pat. No. 3,506,676 or a solid supported tetrathionate.

Step d) Deprotection

Suitable 5'-protection group include, but are not limited to trityl groups, preferably a dimethoxytrityl group (DMTr) or a monomethoxytrityl group (MMTr). These protection groups are used in conventional prior art solid phase oligonucleotides synthesis. Other suitable 5'-protection groups include, but are not limited to is tert-butyl dimethylsilyl (TBDMS), levulinyl, benzoyle, fluorenemethoxycarbonyl (FMOC), the 9-phenylthioxanthen-9-yl (S-pixyl).

In the second embodiment, in step d) the 3'-protection group is removed. Suitable 3'-protection groups include, but are not limited to 3'-O-tert butyl dimethyl silyl (TBDMS), 3'-O-acetate, 3'-O-levulinyl groups. They can be removed by a solid-supported ammonium fluoride, solid-supported ammonium hydroxide or solid-supported hydrazine.

In step d) of the first embodiment, the 5'-protection group is removed. Thereafter the oligonucleotides can either be used or the oligonucleotide corresponds to the 3'-protected compound of step a) to repeat the cycle.

The use of solid supported reagents for the removal of the DMTr-protection group for a completely synthesized oligonucleotide has already been reported in U.S. Pat. No. 5,808,042. The content of this document is incorporated by reference. Surprisingly the methods disclosed in U.S. Pat. No. 5,808,042 can also be applied in a solution phase synthesis as described in the present application.

Suitable reagents are also disclosed in synthetic communications 24 (17) 1994, 2323-2428.

In step d) of the second embodiment, the 3'-protection group is removed. Thereafter the oligonucleotides can either be used or the oligonucleotide corresponds to the 5'-protected compound of step a) to repeat the cycle.

Step e): Repetition

In most cases the methods will be repeated at least once. When starting from monomeric oligonucleotides the method of the present invention will result in a dimer. Repeating the method of the present invention will elongate the dimer to a trimer. By repeating the method of the invention several times n-mers can be synthesized.

As the yield of a synthesis is not 100%, the overall yield of correct oligonucleotides decreases with the number of cycles. Depending on the yield of a single cycle, oligonucleotides can be synthesized of at least up to 100 nucleotides in sufficient yield, but longer oligonucleotides are also possible.

For most cases oligonucleotides having that size will not be needed. An antisense therapy oligonucleotides are normally in the range of 8-36 nucleotides, more preferably 12-30, most commonly in the range of the 16-26 nucleotides.

In contrast to prior art, convergent synthesis strategies are fully compatible with the synthesis method of the present invention. Convergent synthesis methods are methods wherein small oligonucleotides are synthesized first and the small oligonucleotides are then combined for synthesizing larger blocks. By this method the number of coupling reactions can be significantly reduced. Thereby the overall yield of the oligonucleotide is increased.

In prior art, each synthesis of a small oligonucleotide had to start from the solid support bound nucleic acid which was rather expensive. Therefore convergent synthesis strategies have not found much application in oligonucleotide synthesis.

Convergent synthesis has the further advantage, that the reaction product is essentially free of (n−1)mers. In prior art synthesis, the purification of oligonucleotides with a length of n from oligonucleotides with a length of n−1 is the most difficult in purification of the oligonucleotide. By convergent synthesis, these (n−1)mers are nearly avoided, because larger fragments are combined.

In a preferred embodiment, the method of the present invention uses dimers or trimers as the compounds in step a) and/or b).

During the synthesis cycles, reagents are mostly added in a solid supported form. These solid supported reagents are preferably removed after reaction or after each reaction step. Depending on the type of reagent it is in some cases possible to remove two or more of the solid supported reagents together.

In a preferred embodiment, coupling and at least final oxidizing steps are done by solid supported reagents.

As the synthesis is intended for the production of large amounts of oligonucleotides it is preferred that the solid supported reagent is recycled. This recycling is obviously easier if the solid supported reagents are removed separately after each reaction.

The solid supported reagents can be removed by methods like filtration or centrifugation. Because of the ease of handling, filtration is the preferred way of removing the solid supported reagents.

A very preferred reagent for the sulfurization is a solid supported anion exchange resin in complex with a tetrathionate having the formula $S_4O_6$, preferably a quaternary ammonium resin bearing tetrathionate as counter ion.

Purification

After the final synthesis cycle, it will in most cases be necessary to make one or more additional purification steps. Such purification steps for crude oligonucleotide synthesis products are known in prior art solid phase synthesis, It is necessary to remove the remaining protection groups especially from the heterocyclic bases and optionally remaining protecting groups on the sugar or phosphorous backbone.

In a preferred embodiment, in case of the use of MMT or DMT as a protection group, the oligonucleotide is purified by binding to an ion exchanger and the protection group is removed while the oligonucleotide is bound to the exchanger. After removal of the protection groups, the oligonucleotide is released from the ion exchanger.

The invention will be further exemplified with the following examples.

EXAMPLE 1

Synthesis of the dimer
5'-O-DMTr-T-T-3'-O-TBDMS cyanoethyl phosphite triester coupling procedure of 5'-O-DMTr-T-3'-cyanoethyl phosphoramidite with 5'-OH-T-3'-O-TBDMS using the DOWEX 50W X8 pyridinium form.

Analytical Scale.

5'-OH-T-3'-O-TBDMS (11 mg, 32.5 mmol) and 5'-O-DMTr-T-3'-cyanoethyl phosphoramidite (41 mg, 55.25 mmol, 1.7 eq) are dissolved in anhydrous acetonitrile (550 ml). The solution is transferred under argon in a NMR tube containing the DOWEX 50W X8 pyridinium form (100 mg, 0.30 mmol pyrH$^+$, 9.2 eq). The reaction is followed by $^{31}$P NMR. Before the NMR experiment deuterated acetonitrile (50 ml) is added. The yield is determined by $^{31}$P NMR. After 3 h the desired dimer T-T phosphite triester is obtained with 100% of yield compared to 5'-OH-T-3'-O-TBDMS. The crude is a mixture of 5'-O-DMTr-T-3'-cyanoethyl phosphoramidite ($^{31}$P NMR (CD$_3$CN) δ 149.14, 149.07, 14.7%), 5'-O-DMTr-T-T-3'-O-TBDMS cyanoethyl phosphite triester (δ 140.53, 70.2%), 5'-O-DMTr-T-3'-cyanoethyl hydrogenophosphonate (δ 8.74, 15.1%).

EXAMPLE 2

Synthesis of the dimer
5'-O-DMTr-T-T-3'-O-TBDMS cyanoethyl phosphite triester

Coupling procedure of 5'-O-DMTr-T-3'-cyanoethyl phosphoramidite with 5'-OH-T-3'-O-TBDMS using the poly(4-vinylpyridinum p-toluenesulfonate) (Aldrich).

Analytical Scale.

5'-OH-T-3'-O-TBDMS (11 mg, 32.5 mmol) and 5'O-DMTr-T-3'-cyanoethyl phosphoramidite (41 mg, 55.25 mmol, 1.7 eq) are dissolved in anhydrous acetonitrile (550 ml). The solution is transferred under argon in a NMR tube containing the poly(4-vinylpyridinum p-toluenesulfonate) (100 mg, 0.33 mmol tos$^-$, 10.3 eq). The reaction is followed by $^{31}$P NMR. Before the NMR experiment deuterated acetonitrile (50 ml) is added. The yield is determined by $^{31}$P NMR. After 1 h 45 the desired dimer T-T phosphite triester is obtained with 82% of yield compared to 5'-OH-T-3'-P-TBDMS. The crude is a mixture of 5'-O-DMTr-T-T-O-TBDMS cyanoethyl phosphite triester ($^{31}$P NMR (CD$_3$CN) δ 140.54, 48.2%), 5'-O-DMTr-T-3'-cyanoethyl hydrogenophosphonate (δ 8.77, 51.8%).

EXAMPLE 3

Synthesis of the dimer 5'-OH-T-T-3'-O-TBDMS cyanoethyl phosphorothloate triester Coupling procedure of 5'-O-DMTr-T-3'-cyanoethyl phosphoramidite with 5'-OH-T-3'-O-TBDMS using the DOWEX 50W X8 pyridinium form.

A solution of 5'-OH-T-3'-O-TBDMS (124 mg, 0.35 mmol) and 5'-O-DMTr-T-3'-cyanoethyl phosphoramidite (441 mg, 0.59 mmol, 1.7 eq) in anhydrous acetonitrile (6 ml) is added to DOWEX 50W X8 pyridinium form (1 g, 3 mmol pyrH$^+$, 9.5 eq). The resulting mixture is shaken for 4 h 45. The reaction is followed by $^{31}$P NMR and the yield is also determined by $^{31}$P NMR. The desired dimer 5'-O-DMTr-T-T-3'-O-TBDMS cyanoethyl phosphite triester is obtained with 100% of yield compared to 5'-OH-T-3'-O-TBDMS. The crude is a mixture of 5'-O-DMTr-T-3'-cyanoethyl phosphoramidite ($^{31}$P NMR (CD$_3$CN) δ 149.17, 149.10, 5.4%), 5'-O-DMTr-T-T-3'-O-TBDMS cyanoethyl phosphite triester (δ 140.57, 140.54, 68.3%), 5'-O-DMTr-T-3'-cyanoethyl hydrogenophosphonate (δ 8.75, 8.71, 26.3%).

Sulfurization: The DOWEX 50W X8 resin is filtered off and the resulting solution is added to AMBERLYST A26 tetrathionate form (1.44 g, 2.44 mmol $S_4O_6^{2-}$, 7 eq.). The reaction is followed by $^{31}$P NMR and the yield is also determined by $^{31}$P NMR. After 20 h the desired dimer 5'-O-DMTr-T-T-3'-O-TBDMS cyanoethyl phosphorothioate triester is obtained with 97% of yield. The crude is a mixture of 5'-O-DMTr-T-3'-cyanoethyl thiophosphoramidate ($^{31}$P NMR (CD$_3$CN) δ 71.16, 4.0%), 5'-O-DMTr-T-T-3'-O-TBDMS cyanoethyl phosphorothioate tri-ester (d 68.28, 68.23, 69.5%), 5'-O-DMTr-T-3'-cyanoethyl hydrogenophosphonate (d 8.75, 8.71, 26.5%). MALDI-TOF MS (negative mode, trihydroxyacetophenone as matrix) ammonia treatment of an aliquot gives 5'-OH-T-T-3'-O-TBDMS phosphorothioate diester: [M–H]$^-$ m/z$_{exp}$=978.12, m/z$_{calc}$=977.13.

Detritylation: The AMBERLYST A26 is filtered off and the solvent are evaporated. The crude is dissolved in 4 ml of CH$_2$Cl$_2$/CH$_3$OH (7/3) and cooled in an ice bath. To this solution is added 1 ml of a solution of benzene sulfonic acid 10% in CH$_2$Cl$_2$/CH$_3$OH (7/3). The solution is stirred 15 min at 0° C. The reaction is washed with 10 ml of a saturated solution of NaHCO$_3$, the organic layer is separated, dried (Na$_2$SO$_4$), evaporated, and purified on a silica gel column. The desired dimer T-T is eluted with CH$_2$O$_2$/CH$_3$OH (95/5). The appropriates fractions are collected and evaporated to give 230 mg of a white foam in a yield of 83% compared to 5'-OH-T-3'-O-TBDMS. $^{31}$P NMR (CD$_3$CN) δ 68.29, 68.19. MALDI-TOF MS (positive mode, trihydroxyacetophenone as matrix) [M+H]$^+$ m/z$_{exp}$=730.46, m/z$_{calc}$=730.82. The spectrophotometric purity (97%) is determined by HPLC at 260 nm.

EXAMPLE 4

Synthesis of the Trimer Cyanoethyl Phosphorothioate triester

Coupling procedure of 5'-O-DMTr-T-3'-cyanoethyl phosphoramidite with the dimer 5'-OH-T-T-3'-O-TBDMS cyanoethyl phosphorothioate triester using the DOWEX 50W X8 pyridinium form.

A solution of 5'-OH-T-T-3'-O-TBDMS cyanoethyl phosphorothioate triester (230 mg, 0.31 mmol) and 5'-O-DMTr-T-3'-cyanoethyl phosphoramidite (399 mg, 0.54 mmol, 1.7 eq) in anhydrous acetonitrile (8 ml) is added to DOWEX 50W X8 pyridinium form (1 g, 3 mmol pyrH$^+$, 9.5 eq). The resulting mixture is shaken for 5 h. The reaction is followed by $^{31}$P NMR and the yield is also determined by $^{31}$P NMR. The desired trimer 5'-O-DMTr-T-T-T-3'-O-TBDMS cyanoethyl phosphite triester is obtained with 100% of yield compared to the dimer 5'-OH-T-T-3'-O-TBDMS cyanoethyl phosphorothioate triester. The crude is a mixture of 5'-O-DMTr-T-3'-cyanoethyl phosphoramidite ($^{31}$P NMR (CD$_3$CN) δ 149.16, 149.10, 17.7%), 5'-O-DMTr-T-T-T-3'-O-TBDMS cyanoethyl phosphite triester (δ 140.85, 140.68, 140.37, 140.30, d 68.07, 68.02, 68.3%), 5'-O-DMTr-T-3'-cyanoethyl hydrogenophosphonate (88.7, 8.68, 14%).

Sulfurization: The DOWEX 50W X8 pyridinium form is filtered off and the resulting solution is added to AMBERLYST A26 tetrathionate form (1.3 g, 2.44 mmol S$_4$O$_6^{2-}$, 7 eq.). The reaction is followed by $^{31}$P NMR and the yield is also determined by $^{31}$P NMR. After 45 h the desired trimer 5'-O-DMTr-T-T-T-3'-O-TBDMS cyanoethyl phosphorothioate triester is obtained with 100% of yield. MALDI-TOF MS (negative mode, trihydroxyacetophenone as matrix) [M–H]$^-$ m/z$_{exp}$=1297.89, m/z$_{calc}$=1296.38 after 30 min of ammonia treatment to remove the cyanoethyl protecting group, The crude is a mixture of 5'-O-DMTr-T-3'-cyanoethyl thiophosphoramidate ($^{31}$P NMR (CD$_3$CN) d 72.04, 71.17, 14.0%), 5'-O-DMTr-T-T-T-3'-O-TBDMS cyanoethyl phosphorothioate triester (d 68.17, 68.12, 68.07, 67.96, 67.80, 67.58, 73.8%), 5'-O-DMTr-T-3'-cyanoethyl hydrogenophosphonate (d 8.76, 8.71, 12.2%).

Detritylation: The AMBERLYST A26 is filtered off and the solvent are evaporated. The crude Is dissolved in 4 ml of CH$_2$Cl/CH$_3$—OH (7/3) and cooled in an ice bath. To this solution is added 1 ml of a solution of benzene sulfonic acid 10% in CH$_2$Cl/CH$_3$OH (7/3). The solution is stirred 45 min at 0° C. The reaction is washed with 10 ml of a saturated solution of NaHCO$_3$, the organic layer is separated, dried (Na$_2$SO$_4$), evaporated, and purified on a silica gel column. The desired trimer T-T-T is eluted with CH$_2$Cl/CH$_3$OH (95/5). The appropriates fractions are collected and evaporated to give 221 mg of a white foam in a yield of 63% compared to the dimer 5'-OH-T-T-3'-O-TBDMS cyanoethyl phosphorothioate triester. $^{31}$P NMR (CD$_3$CN) δ 68.53, 68.38, 68.34, 67.74, 67.54. MALDI-TOF MS (positive mode, trihydroxyacetophenone as matrix) [M+H]$^+$ m/z$_{exp}$=1103.91, m/z$_{calc}$=1104.15. The spectrophotometric purity (93%) is determined by HPLC at 260 nm.

EXAMPLE 5

Synthesis of the dimer 5'-OH-T-dA$^{Bz}$-3'O-TBDMS cyanoethyl phosphorothioate triester Coupling procedure of 5'-O-DMTr-T-3'-phosphoramidite with 5'-OH-dA$^{Bz}$-3'-O-TBDMS using the poly(4-vinylpyridinum p-toluenesulfonate) (Aldrich).

A solution of 5'-OH-dA$^{Bz}$-3'-O-TBDMS (176 mg, 0.38 mmol) and 5'-O-DMTr-T-3'-cyanoethyl phosphoramidite (560 mg, 0.75 mmol, 2 eq) in anhydrous acetonitrile (6 ml) is added to poly(4-vinylpyridinum p-toluenesulfonate) (1.15 g, 3.84 mmol tos$^-$, 10.2 eq). The resulting mixture is shaken for 4 h 30 min. The reaction is followed by $^{31}$P NMR and the yield is also determined by $^{31}$P NMR. The desired dimer 5'-O-DMTr-T-dA$^{Bz}$-3'-O-TBDMS cyanoethyl phosphite triester is obtained with 100% of yield compared to the 5'-OH-dA$^{Bz}$-3'-O-TBDMS. The crude is a mixture of 5'-O-DMTr-T-3'-cyanoethyl phosphoramidite ($^{31}$P NMR (CD$_3$CN) δ 149.10, 149.05, 12.3%), 5'-O-DMTr-T-A$^{Bz}$-3'-O-TBDMS cyanoethyl phosphite triester (δ 140.52, 140.37, 50%), 5'-O-DMTr-T-3'-cyanoethyl hydrogenophosphonate (δ 8.72, 8.69, 37.7%).

Sulfurization: The poly(4-vinylpyridinum p-toluenesulfonate) is filtered off and the resulting solution is added to AMBERLYST A26 tetrathionate form (1.55 g, 2.63 mmol S$_4$O$_6^{2-}$, 7 eq.). The reaction is followed by $^{31}$P NMR. The reaction mixture is shaken for 24 h 30. The desired dimer 5'-O-DMTr-T-dA$^{Bz}$-3'-O-TBDMS cyanoethyl phosphorothioate triester is isolated after filtration of the resin, evaporation of the solvent, and column chromatography (silica gel; CH$_2$Cl/MeOH (50/1)). Yield: 325 mg, 0.28 mmol, 76%. $^{31}$P NMR (CD$_3$CN) δ 68.34, 68.15. MALDI-TOF (positive mode, trihydroxyacetophenone as matrix) [M+H]$^+$ m/z$_{exp}$=1144.22, m/z$_{calc}$=1146.32.

Detritylation: The 5'-O-DMTr-T-dA$^{Bz}$-3'-O-TBDMS cyanoethyl phosphorothioate triester is dissolved in 10 ml of CH$_2$Cl$_2$/CH$_2$OH (7/3) and cooled in an ice bath. To this solution is added 1 ml of a solution of benzene sulfonic acid 10% in CH$_2$Cl/CH$_3$OH (7/3). The solution is stirred 35 min at 0° C. The reaction is washed with 20 ml of a saturated solution of NaHCO$_3$, the organic layer is separated, dried (Na$_2$SO$_4$), evaporated, and purified on a silica gel column. The desired dimer T-dA$^{Bz}$ is eluted with CH$_2$Cl/CH$_3$OH (95/5). The appropriates fractions are collected and evaporated to give a white foam. Yield: 223 mg, 0.26 mmol, 71%. $^{31}$P NMR (CD$_3$CN) δ 68.06, 67.89. MALDI-TOF MS (positive mode, trihydroxyacetophenone as matrix) [M–H]$^+$ m/z$_{exp}$=842.18, m/z$_{calc}$=843.95; (negative mode, trihydroxyacetophenone as matrix) ammonia treatment of an aliquot gives 5'-OH-T-dA-3'-O-TBDMS phosphorothioate diester: [M–H]$^-$ m/z$_{exp}$=685.38, m/z$_{calc}$=684.77.

EXAMPLE 6

Synthesis of the trimer 5'-O-DMTr-dA$^{Bz}$-3'-O-TBDMS Cyanoethyl phosphorothioate Triester Coupling procedure of 5'-O-DMTr-dA$^{Bz}$-3'-cyanoethyl phosphoramidite with the dimer 5'-OH-T-A$^{Bz}$-3'-O-TBDMS phosphorothioate triester using the poly(4-vinylpyridinum p-toluenesulfonate) (Aldrich), A solution of the dimer 5'-OH-T-dA$^{Bz}$-3'-O-TBDMS phosphorothioate triester (223 mg, 0.26 mmol) and 5'-O-DMTr-dA$^{Bz}$-3'-cyanoethyl phosphoramidite (432 mg, 0.50 mmol, 1.9 eq) in anhydrous acetonitrile (20 ml) is added to poly(4-vinylpyridinum p-toluenesulfonate) (0.8 g, 2.7 mmol tos$^-$, 10.3 eq). The resulting mixture is shaken for 6 h 30. The reaction is followed by $^{31}$P NMR and the yield is also determined by $^{31}$P NMR. The desired trimer 5'-O-DMTr-dA$^{Bz}$-T-dA$^{Bz}$-3'-O-TBDMS cyanoethyl phosphite triester is obtained with 62% of yield compared to the dimer 5'-OH-T-dA$^{Bz}$-3'-O-TBDMS phosphorothioate triester. The crude is a mixture of 5'-O-DMTr-dA$^{Bz}$-3'-cyanoethyl phosphoramidite ($^{31}$P NMR (CD$_3$CN) d 149.14, 8.4%), 5'-O-DMTr-dA$^{Bz}$-T-dA$^{Bz}$-3'-O-TBDMS cyanoethyl phosphite triester δ (140.90, 140.77, 67.85, 67.79, 43.3%), 5'-OH-T-dA$^{Bz}$-3'-O-TBDMS phosphorothioate triester (δ 68.03, 67.89, 13.4%), 5'-O-DMTr-dA$^{Bz}$-3'-cyanoethyl hydrogenophosphonate (δ 8.71, 8.66, 34.9%).

Sulfurization: The poly(4-vinylpyridinum p-toluenesulfonate) is filtered off and the resulting solution is added to AMBERLYST A26 tetrathionate form (0.78 g, 1.33 mmol S$_4$O$_6^{2-}$, 5 eq.). The reaction is followed by $^{31}$P NMR and the yield is also determined by $^{31}$P NMR. After 14 h 30 the desired trimer 5'-O-DMTr-dA$^{Bz}$-T-dA$^{Bz}$-3'-O-TBDMS cyanoethyl phosphorothioate triester is obtained with 100% of yield. The crude is a mixture of 5'-O-DMTr-dA$^{Bz}$-3'-cyanoethyl thiophosphoramidate ($^{31}$P NMR (CD$_3$CN) d 71.88, 71.21, 10%), 5'-O-DMTr-dA$^{Bz}$-T-dA$^{Bz}$-3'-O-TBDMS cyanoethyl phosphorothioate triester (25.9%) and 5'-OH-T-dA$^{Bz}$-3'-O-TBDMS cyanoethyl phosphorothioate triester (16.2%) (δ 68.08, 68.05, 67.93, 67.89, 67.85, 67.79, 67.57), 5'-O-DMTr-T-3'-cyanoethyl phosphorothioate diester (δ 57.38, 4.8%), 5'-O-DMTr-dA$^{Bz}$-3'-cyanoethyl hydrogenophosphonate (δ 8.75, 8.70, 43.11%). MALDI-TOF MS (positive mode, trihydroxyacetophenone as matrix) [M+H]$^+$ m/z$_{exp}$=1631.68, m/z$_{calc}$=1632.77; (negative mode, trihydroxyacetophenone as matrix) ammonia treatment of an aliquot gives 5'-OH-T-dA-3'-O-TBDMS phosphorothioate diester: [M−H]$^-$ m/z$_{exp}$=1316.45, m/z$_{calc}$=1316.43.

EXAMPLE 7

Synthesis of the dimer 5'''-O-DMTr-dC$^{Bz}$-T-3'-O-Lev cyanoethyl phosphite triester Coupling procedure of 5'-O-DMTr-dC$^{Bz}$-3'-cyanoethyl phosphoramidite with 5'-OH-T-3'-O-Lev using the DOWEX 50W XS pyridinium form.

Analytical Scale.

5'-OH-T-3'-O-Lev (20 mg, 58.9 mmol) and 5'-O-DMTr-dC$^{Bz}$-3'-cyanoethyl phosphoramidite (83.4 mg, 100 mmol, 1.7 eq) are dissolved in anhydrous acetonitrile (550 ml). The solution is transferred under argon in a NMR tube containing the DOWEX 50W X8 pyridinium form (181 mg, 0.54 mmol pyrH$^+$, 9.2 eq). The reaction is followed by $^{31}$P NMR. Before the NMR experiment deuterated acetonitrile (50 ml) is added. The yield is determined by $^{31}$P NMR. After 6 h the desired dimer T-dC$^{Bz}$ phosphite triester is obtained with 100% of yield compared to 5'-OH-T-3'-O-Lev. The crude is a mixture of 5'-O-DMTr-dC$^{Bz}$-3'-cyanoethyl phosphoramidite ($^{31}$P NMR (CD$_3$CN) δ 149.36, 149.32, 11%), 5'-O-DMTr-T-dC$^{Bz}$-3'-O-TBDMS cyanoethyl phosphite triester (δ 140.52, 140.39, 70%), 5'-O-DMTr-dC$^{Bz}$-3'-cyanoethyl hydrogenophosphonate (δ 8.90, 8.58, 19%).

EXAMPLE 8

Synthesis of the dimer 5'-OH-dC$^{Bz}$-T-3'-O-Lev Cyanoethyl Phosphorothioate Triester Coupling procedure of 5'-O-DMTr-dC$^{Bz}$-3'-cyanoethyl phosphoramidite with 5'-OH-T-3'-O-Lev using the DOWEX 50W X8 pyridinium form.

A solution of 5'-OH-T-3'-O-Lev (119 mg, 0.35 mmol) and 5'-O-DMTr-dC$^{Bz}$-3'-cyanoethyl phosphoramidite (496 mg, 0.60 mmol, 1.7 eq) in anhydrous acetonitrile (10 ml) is added to DOWEX 50W X8 pyridinium form (1.1 g, 3.3 mmol pyrH$^+$, 9.4 eq). The resulting mixture is shaken for 5 h 30 min. The reaction is followed by $^{31}$P NMR and the yield is also determined by $^{31}$P NMR. The desired dimer 5'-O-DMTr-dC$^{Bz}$-T-3'-O-Lev cyanoethyl phosphite triester is obtained with 100% of yield compared to 5'-OH-T-3'-O-Lev. The crude is a mixture of 5'-O-DMTr-T-dC$^{Bz}$-T-3'-O-Lev cyanoethyl phosphite triester ($^{31}$P NMR (CD$_3$CN) δ 140.59, 140.45, 64%), 5'-O-DMTr-dC$^{Bz}$-3'-cyanoethyl hydrogenophosphonate (δ 8.68, 8.66, 36%).

Sulfurization: The DOWEX 50W X8 resin is filtered off and the resulting solution is added to AMBERLYST A26 tetrathionate form (1.44 g, 2.44 mmol S$_4$O$_6^{2-}$, 7 eq.). The reaction is followed by $^{31}$P NMR. The reaction mixture is shaken for 16 h. The desired dimer 5'-O-DMTr-dC$^{Bz}$-T-3'-O-Lev cyanoethyl phosphorothioate triester is isolated after filtration of the resin, evaporation of the solvent and column chromatography (silica gel; CH$_2$Cl$_2$/MeOH (97/3)). The crude is a mixture of 5'-O-DMTr-T-dC$^{Bz}$-3'-O-Lev cyanoethyl phosphorothioate triester ($^{31}$P NMR (CD$_3$CN) δ 68.05, 67.89, 83.7%), 5'-O-DMTr-dC$^{Bz}$-3'-cyanoethyl hydrogenophosphonate (δ 8.63, 16.3%). The spectrophotometric purity determined by HPLC at 260 nm is 80%.

Detrytilation of the dimer 5'-O-DMTr-dC$^{Bz}$-T-3'-O-Lev cyanoethyl phosphorothioate triester with the DOWEX 50 W×8H$^+$ form (Aldrich).

To the mixture of the dimer 5'-O-DMTr-dC$^{Bz}$-T-3'-O-Lev cyanoethyl phosphorothioate triester (121 mmol estimated) and 5'-O-DMTr-T-3'-cyanoethyl hydrogenophosphonate diester (44 mmol estimated) in solution in 10 ml of CH$_2$Cl/MeOH (7/3) is added the DOWEX 50 W×8H$^+$ form (1.4 g, 7 mmol H$^+$, 58 eq/dimer). The reaction is followed by reverse phase HPLC. After 15 min the detritylation is complete. The resin is filtered off and the solvents are evaporated. The desired dimer 5'-OH-dC$^{Bz}$-T-3'-O-Lev cyanoethyl phosphorothioate triester is purified by precipitation from CH$_2$Cl$_2$/MeOH (9/1) in diethylether. $^{31}$P NMR (CD$_3$OD) δ 68.24, 67.90, MALDI-TOF MS (positive mode, trihydroxyacetophenone as matrix) [M−H]$^+$ m/z$_{exp}$=803.11 m/z$_{calc}$=803.76, The spectrophotometric purity (97%) is determined by HPLC at 260 nm.

EXAMPLE 9

Synthesis of the dimer cyanoethyl phosphorothioate triester

Coupling procedure of 5'-O-DMTr-T-3'-cyanoethyl phospharamidite with 5'-OH-T-3'-O-Lev using the DOWEX 50W X8 pyridinium form.

A solution of 5'-OH-T-3'-O-Lev (100 mg, 0.29 mmol) and 5'-O-DMTr-T-3'-cyanoethyl phosphoramidite (547 mg, 0.73 mmol, 2.5 eq) in anhydrous acetonitrile (10 ml) is added to DOWEX 50W X8 pyridinium form (0.9 g, 2.7 mmol pyrH$^+$, 9.3 eq). The resulting mixture is shaken for 10 h. The reaction is followed by $^{31}$P NMR and by reverse phase HPLC. The excess of 5'-O-DMTr-T-3'-cyanoethyl phosphoramidite is hydrolysed with 500 ml of water The desired dimer 5'-O-DMTr-T-T-3'-O-Lev cyanoethyl phosphite triester is obtained with 100% of yield compared to 5'-OH-T-3'-O-Lev. The crude is a mixture of 5'-O-DMTr-T-T-3'-O-Lev cyanoethyl phosphite triester (HPLC % Area=55%) and 5'-O-DMTr-T-3'-cyanoethyl hydrogenophosphonate (HPLC % Area=45%).

Sulfurization: The DOWEX 50W X8 resin is filtered off and the resulting solution is added to AMBERLYST A26 tetrathionate form (0.8 g, 1.5 mmol $S_4O_6^{2-}$, 5 eq.). The reaction is followed by $^{31}P$ NMR and by reverse phase HPLC. After 15 h the desired dimer 5'-O-DMTr-T-T-3'-O-Lev cyanoethyl phosphorothioate triester is obtained with 100% of yield. The crude is a mixture of 5'-O-DMTr-T-T-3'-O-Lev cyanoethyl phosphorothioate triester ($^{31}P$ NMR d 68.04, HPLC % Area=57%), 5'-O-DMTr-T-3'-cyanoethyl hydrogenophosphonate (d 8.77, HPLC % Area=43%).

Detrytilation of the dimer 5'-O-DMTr-T-T-3'-O-Lev cyanoethyl phosphorothioate triester with the DOWEX 50 W×8H$^+$ form (Aldrich).

The AMBERLYST A26 resin is filtered off and the solvents are evaporated. To the mixture of the dimer 5'-O-DMTr-T-T-3'-O-Lev cyanoethyl phosphorothioate triester (0.29 mmol estimated) and 5'-O-DMTr-T-3'-cyanoethyl hydrogenophosphonate (0.22 mmol estimated) in solution in 20 ml of $CH_2O_2$/MeOH (7/3) is added the DOWEX 50 W×8H$^+$ form (3.7 g, 18.5 mmol H$^+$, 64 eq/dimer). The reaction is followed by reverse phase HPLC. After 30 min the detrytilation of the dimer is complete. The resin is filtered off and the solvents are evaporated. The desired dimer 5'-OH-T-T-3'-O-Lev cyanoethyl phosphorothioate triester is purified by precipitation from $CH_2Cl$/MeOH (9/1) in diethylether. $^{31}P$ NMR ($CD_3CN$) d 67.88, 67.73. MALDI-TOF MS (positive mode, trihydroxyacetophenone as matrix) [M-H]$^+$ m/$z_{exp}$=713.79 m/$z_{calc}$=714.66. The purity (95%) is determined by HPLC.

EXAMPLE 10

Synthesis of dimer 5'-O-DMTr-dA$^{Bz}$-dA$^{Bz}$-3'-O-TBDMS Cyanoethyl Phosphorothioate Triester Dimer Coupling procedure of 5'-O-DMTr-dA$^{Bz}$-3'-cyanoethyl-phosphoramidite with 5'-OH-dA$^{Bz}$-3'-O-TBDMS using the DOWEX SOW X8 pyridinium form:

5'-OH-dA$^{Bz}$-3'-O-TBDMS (100 mg, 0.21 mmol) and 5'-O-DMTr-dA$^{Bz}$-3'-cyanoethyl-phosphoramidite (311 mg, 0.36 mmol, 1.7 eq) are dissolved in anhydrous acetonitrile (15 ml). The solution is transferred under argon in a flask containing the DOWEX 50W X8 pyridinium form (655 mg, 1.97 mmol pyrH$^+$, 9.2 eq) and is shaken for 4 h 30 min. The reaction is followed by $^{31}P$ NMR. The yield is determined by $^{31}P$ NMR. The desired dA-dA phosphite triester dimer is obtained with 92% of yield compared to the 5'-OH-dA$^{Bz}$-3'-O-TBDMS. The crude is a mixture of 5'-O-DMTr-dA$^{Bz}$-3'-cyanoethyl phosphoramidite ($^{31}P$ NMR ($CD_3CN$) δ 149.25, 149.13; 27.7%), 5'-O-DMTr-dA$^{Bz}$-dA$^{Bz}$-3'-O-TBDMS cyanoethyl phosphite triester (δ 140.75, 140.38; 53.9%), 5'-O-DMTr-dA$^{Bz}$-3'-cyanoethyl hydrogenophosphonate (δ 8.69, 8.64; 18.5%).

Sulfurization: To a solution of 5'-O-DMTr-dA$^{Bz}$-dA$^{Bz}$-3'-O-TBDMS phosphite triester dimer (0.2 mmol) in anhydrous acetonitrile is added AMBERLYST A26 tetrathionate form (5.4 eq., 1.14 mmol $S_4O_6^{2-}$, 0.63 g). The reaction mixture is shaken for 20 h. The reaction is followed by $^{31}P$ NMR, The yield is determined by $^{31}P$ NMR. After filtration of the resins the desired dimer dA-dA phosphorothioate triester is obtained with 88% of yield compared to the 5'-OH-dA$^{Bz}$-3'-O-TBDMS. The crude is a mixture of 5'-O-DMTr-dA$^{Bz}$-3'-cyanoethyl thiophosphoramidate ($^{31}P$ NMR ($CD_3CN$) δ 71.85, 71.22; 29.0%), 5'-O-DMTr-dA$^{Bz}$-dA$^{Bz}$-3'-O-TBDMS cyanoethyl phosphorothioate (δ 68.08, 68.01; 51.5%), 5'-O-DMTr-de-3'-cyanoethyl hydrogenophosphonate (δ 8.66, 8.59; 19.5%).

EXAMPLE 11

Synthesis of the dimer 5'-OH-dC$^{Bz}$-dA$^{Bz}$-3'-O-TBDMS Cyanoethyl Phosphorothioate Triester Coupling procedure of 5'-O-DMTr-dC$^{Bz}$-3'-cyanoethyl-phosphoramidite with 5'-OH-dA$^{Bz}$-3'-O-TBDMS using the poly(4-vinylpyridinum p-toluenesulfonate) (Aldrich):

5'-OH-dA$^{Bz}$-3'-O-TBDMS adenosine (100 mg, 0.21 mmol) and 5'-O-DMTr-dC$^{Bz}$-3'-cyanoethyl-phosphoramidite (365 mg, 0.43 mmol, 2. eq) are dissolved in anhydrous acetonitrile (15 ml). The solution is transferred under argon in a flask containing the poly(4-vinylpyridinum p-toluenesulfonate) (655 mg, 2.17 mmol tos$^-$, 10.2 eq) and is shaken for 5 h 50 min. The reaction is followed by $^{31}P$ NMR. The yield is determined by $^{31}P$ NMR. The desired dC-dA phosphite triester dimer is obtained with 100% of yield compared to the 5'-OH-dA$^{Bz}$-3'-O-TBDMS. The crude is a mixture of 5'-O-DMTr-dC$^{Bz}$-dA$^{Bz}$-3'-O-TBDMS cyanoethyl phosphite triester ($^{31}P$ NMR ($CD_3CN$) (δ 140.55, 140.49; 53.9%), 5'-O-DMTr-dC$^{Bz}$-3'-cyanoethyl hydrogenophosphonate (δ 8.67; 18.5%).

Sulfurization: To a solution of 5'-O-DMTr-dC$^{Bz}$-dA$^{Bz}$-3'-O-TBDMS cyanoethyl phosphite triester dimer (0.21 mmol) in anhydrous dichloromethane is added AMBERLYST A26 tetrathionate form (0.63 g, 1.14 mmol $S_4O_6^{2-}$, 5.3 eq.). The reaction mixture is shaken for 14 h 30 min. The reaction is followed by $^{31}P$ NMR. The yield is determined by $^{31}P$ NMR. After filtration of the resins the desired phosphorothioate triester dimer is obtained with 100% of yield compared to the 5'OH-dA$^{Bz}$-3'-O-TBDMS. The crude is a mixture of 5'-O-DMTr-dC$^{Bz}$-dA$^{Bz}$-3'-O-TBDMS cyanoethyl phosphorothioate ($^{31}P$ NMR ($CD_3CN$) (d 68.14, 68.07; 50.6%), 5'-O-DMTr-dC$^{Bz}$-3'-cyanoethyl hydrogenophosphonate (d 8.67; 49.4%). Purification is attempted on a silica gel column, which is treated with triethylamine. Chromatography leads to complete loss of the cyanoethyl group. The dC$^{Bz}$-dA$^{Bz}$ phosphorothioate dimer is eluted with $CH_2Cl$/$CH_3OH$ (80/1). The appropriates fractions are collected and evaporated to give a colorless oil. Yield: 185 mg, 0.14 mmol, 68%; $^{31}P$ NMR ($CD_3CN$) d 57.58, 57.45; MALDI-TOF MS (positive mode, trihydroxyacetophenone as matrix) [M-DMTr+2H]$^+$ m/$z_{exp}$=879.42, m/$z_{calc}$=878.97.

EXAMPLE 12

Synthesis of the dimer 5'-OH-dA$^{Bz}$-dA$^{Bz}$-3'-O-TBDMS Cyanoethyl Phosphorothioate Triester Coupling procedure of 5'O-DMTr-dA$^{Bz}$-3'-cyanoethyl-phosphoramidite with 5'-OH-dA$^{Bz}$-3'-O-TBDMS using the poly(4-vinylpyridinum p-toluenesulfonate) (Aldrich):

5'-OH-dA$^{Bz}$-3'-O-TBDMS (102 mg, 0.22 mmol) and 5'-O-DMTr-dA$^{Bz}$-3'-cyanoethyl-phosphoramidite (381 mg, 0.44 mmol, 2.05 eq) are dissolved in anhydrous dichloromethane (15 ml). The solution is transferred under argon in a flask containing the poly(4-vinylpyridinum p-toluenesulfonate) (655 mg, 2.19 mmol tos$^-$, 10.1 eq) and is shaken for 5 h 40 min. The reaction is followed by $^{31}P$ NMR. The yield is determined by $^{31}P$ NMR. The desired dA-dA phosphite triester dimer is obtained with 100% of yield compared to the 5'-OH-dA$^{Bz}$-3'-O-TBDMS. The crude is a mixture of 5'-O-DMTr-dA$^{Bz}$-dA$^{Bz}$-3'-O-TBDMS cyanoethyl phosphite triester ($^{31}P$ NMR (CD$_3$CN) (d 140.77, 140.46; 66.9%), 5'-O-DMTr-dA$^{Bz}$-3'-cyanoethyl hydrogenophosphonate (d 8.50, 8.41; 33.1%).

Sulfurization: To a solution of 5'-O-DMTr-dA$^{Bz}$-dA$^{Bz}$-3'-O-TBDMS cyanoethyl phosphite triester dimer (0.22 mmol) in anhydrous dichloromethane is added AMBERLYST A26 tetrathionate form (0.87 g, 1.14 mmol S$_4$O$_6^{2-}$, 5.4 eq.). The reaction mixture is shaken for 22 h. The reaction is followed by $^{31}P$ NMR. The yield is determined by $^{31}P$ NMR. After filtration of the resins the desired dA-dA phosphorothioate triester dimer is obtained with 100% of yield compared to the 5'-OH-A$^{Bz}$-3'-O-TBDMS. The crude is a mixture of 5'-O-DMTr-dA$^{Bz}$-dA$^{Bz}$-3'-O-TBDMS cyanoethyl phosphorothioate ($^{31}P$ NMR (CD$_3$CN) (d 68.17, 67.89; 62.3%), 5'-O-DMTr-dA$^{Bz}$-3'-cyanoethyl hydrogenophosphonate ($\delta$ 8.45, 8.35; 37.7%).

Detritylation: To a solution of 5'-O-DMTr-dA$^{Bz}$-dA$^{Bz}$-3'-O-TBDMS cyanoethyl phosphorothioate triester (0.22 mmol) in 10 ml CH$_2$Cl/CH$_3$OH (7/3) is added 0.63 ml (0.3 mmol, 1.4 eq.) of a solution of benzene sulfonic acid 10% in CH$_2$Cl/CH$_3$OH (7/3). The solution is stirred 45 min at 0° C. The reaction is washed with 10 ml of a saturated solution of NaHCO$_3$, the organic layer is separated, dried (Na$_2$SO$_4$), evaporated, and purified on a silica gel column. The desired dA-dA dimer is eluted with CH$_2$Cl/CH$_3$OH (33/1). The appropriates fractions are collected and evaporated to give a colorless oil. Yield: 73 mg, 76 mmol, 35%; $^{31}P$ NMR (CD$_3$CN) $\delta$ 67.80, 67.71; MALDI-TOF MS (positive mode, trihydroxyacetophenone as matrix) [M–H]$^+$ m/z$_{exp}$=957.01, m/z$_{calc}$=957.07; HPLC (spectrophotometrical purity at 260 nm=95%).

EXAMPLE 13

Synthesis of the dimer 5'-OH-dG$^{IBu}$-dA$^{Bz}$-3'-O-TBDMS Cyanoethyl Phosphorothioate Triester Coupling procedure of 5'-O-DMTr-dG$^{IBu}$-3'-cyanoethyl-phosphoramidite with 5'-OH-dA$^{Bz}$-3'-O-TBDMS using the poly(4-vinylpyridinum p-toluenesulfonate) (Aldrich):

5'-OH-dA-3'-O-TBDMS (100 mg, 0.21 mmol) and 5'-O-DMTr-dG$^{IBu}$-3'-cyanoethyl-phosphoramidite (352 mg, 0.42 mmol, 1.97 eq) are dissolved in anhydrous acetonitrile (20 ml). The solution is transferred under argon in a flask containing the poly(4-vinylpyridinum p-toluenesulfonate) (655 mg, 2.19 mmol tos$^-$, 10.3 eq) and is shaken for 5 h 30 min. The reaction is followed by $^{31}P$ NMR. The yield is determined by $^{31}P$ NMR. The desired dG-dA phosphite triester dimer is obtained with 100% of yield compared to the 5'-OH-dA$^{Bz}$-3'-O-TBDMS. The crude is a mixture of 5'-O-DMTr-dG$^{IBu}$-dA$^{Bz}$-3'-O-TBDMS cyanoethyl phosphite triester ($^{31}P$ NMR (CDCN) ($\delta$ 140.65, 140.45; 51.2%), 5'-O-DMTr-dG$^{IBu}$-3'-cyanoethyl hydrogenophosphonate ($\delta$ 9.00, 8.81; 48.8%).

Sulfurization: To a solution of 5'-O-DMTr-dG$^{IBu}$-dA$^{Bz}$-3'-O-TBDMS cyanoethyl phosphite triester dimer (0.21 mmol) in anhydrous acetonitrile is added AMBERLYST A26 tetrathionate form (0.63 g, 1.14 mmol S$_4$O$_6^{2-}$, 5.4 eq.). The reaction mixture is shaken for 2 h. The reaction is followed by $^{31}P$ NMR. The yield is determined by $^{31}P$ NMR. After filtration of the resins the desired dG-dA phosphorothioate triester dimer is obtained with 100% of yield compared to the 5'-OH-dA$^{Bz}$-3'-O-TBDMS. The crude is a mixture of 5'-O-DMTr-dG$^{IBu}$-dA$^{Bz}$-3'-O-TBDMS cyanoethyl phosphorothioate ($^{31}P$ NMR (CDCN) ($\delta$ 68.15, 68.02; 50.4%), 5'-O-DMTr-dG$^{IBu}$-3'-cyanoethyl hydrogenophosphonate ($\delta$ 8.91, 8.68; 49.6%).

Detritylation: To a solution of 5'-O-DMTr-dG$^{IBu}$-dA$^{Bz}$-3'-O-TBDMS cyanoethyl phosphorothioate triester (0.21 mmol) in 10 ml CH$_2$Cl/CH$_3$OH (7/3) is added 0.5 ml (0.3 mmol, 1.4 eq.) of a solution of benzene sulfonic acid 10% in CH$_2$Cl/CH$_3$OH (7/3). The solution is stirred 20 min at 0° C. The reaction is washed with 10 ml of a saturated solution of NaHCO$_3$, the organic layer is separated, dried (Na$_2$SO$_4$), evaporated, and purified on a silica gel column. The desired G-A dimer is eluted with CH$_2$Cl$_2$/CH$_3$OH (33/1). The appropriates fractions are collected and evaporated to give a white foam. Yield: 95 mg, 0.1 mmol, 48% with respect of 5'-OH-dA-3'-O-TBDM; $^{31}P$ NMR (CD$_3$CN) $\delta$ 68.10, 67.87; HPLC (spectrophotometrical purity at 260 nm 80%).

EXAMPLE 14

Synthesis of the dimer 5'-OH-dG$^{IBu}$-dC$^{Bz}$-3'-O-TBDMS Cyanoethyl Phosphorothioate Triester Coupling procedure of 5'-O-DMTr-dG$^{IBu}$-3'-cyanoethyl-phosphoramidite with 5'OH-dC$^{Bz}$-3'-O-TBDMS using the poly(4-vinylpyridinum p-toluenesulfonate) (Aldrich):

5'-OH-dC$^{Bz}$-3'-O-TBDMS (100 mg, 0.22 mmol) and 5'-O-DMTr-dG$^{IBu}$-3'-cyanoethyl-phosphoramidite (371 mg, 0.45 mmol, 2 eq) are dissolved in anhydrous acetonitrile (15 ml). The solution is transferred under argon in a flask containing the poly(4-vinylpyridinum p-toluenesulfonate) (690 mg, 2.3 mmol tos$^-$, 10.3 eq) and is shaken for 5 h. The reaction is followed by $^{31}P$ NMR. The yield is determined by $^{31}P$ NMR. The desired dG-dC phosphite triester dimer is obtained with 100% of yield compared to the 5'-OH-dC$^{Bz}$-3'-O-TBDMS. The crude is a mixture of 5'-O-DMTr-dG$^{IBu}$-dC$^{Bz}$-3'-O-TBDMS cyanoethyl phosphite triester ($^{31}P$ NMR (CD$_3$CN) ($\delta$ 141.73, 141.26; 62.1%), 5'-O-DMTr-dG$^{IBu}$-3'-cyanoethyl hydrogeno-phosphonate ($\delta$ 9.05, 8.88; 37.9%).

Sulfurization: To a solution of 5'-O-DMTr-dG$^{IBu}$-dC$^{Bz}$-3'-O-TBDMS cyanoethyl phosphite triester dimer (0.22 mmol) in anhydrous acetonitrile is added AMBERLYST A26 tetrathionate form (0.65 g, 1.3 mmol S$_4$O$_6^{2-}$, 5.4 eq.). The reaction mixture is shaken for 2 h. The reaction is followed by $^{31}P$ NMR. The yield is determined by $^{31}P$ NMR. After filtration of the resins the desired dG-dC phosphorothioate triester dimer is obtained with 100% of yield compared to the 5'OH-dC$^{Bz}$-3'-O-TBDMS. The crude is a mixture of 5'-O-DMTr-dG$^{IBu}$-dC$^{Bz}$-3'-O-TBDMS cyanoethyl phosphorothioate ($^{31}P$ NMR (CD$_3$CN) ($\delta$ 68.12, 67.73; 61.2%), 5'-O-DMTr-dG$^{IBu}$-3'-cyanoethyl phosphorothioate diester ($\delta$ 56.51, 56.39; 25.4%), 5'-O-DMTr-dG$^{IBu}$-3'-cyanoethyl hydrogenophosphonate (d 9.04, 8.85; 25.4%). $^{31}P$ NMR d.

Detritylation: To a solution of 5'-O-DMTr-dG$^{IBu}$-dC$^{Bz}$-3'-O-TBDMS cyanoethyl phosphorothioate triester (0.22 mmol) in 10 ml CH$_2$Cl/CH$_3$OH (7/3) is added 0.5 ml (0.3 mmol, 1.4 eq.) of a solution of benzene sulfonic acid 10% in CH$_2$Cl/CH$_3$OH (7/3). The solution is stirred 1 h at 0° C. The reaction is washed with 10 ml of a saturated solution of NaHCO$_3$, the organic layer is separated, dried (Na$_2$SO$_4$) and evaporated. The crude product is purified on a silica gel column using CH$_2$Cl$_2$/CH$_3$OH (33:1). The appropriate fractions are collected and evaporated to give a colorless oil. Yield: 99 mg, 0.1 mmol, 47%; $^{31}P$ NMR (CD$_3$CN) $\delta$ 67.82, 67.56; MALDI-TOF MS (positive mode, trihydroxyacetophenone as matrix) [M−H]+ m/z$_{exp}$=914.78, m/z$_{calc}$=914.03; HPLC (spectrophotometrical purity at 260 nm=84%).

EXAMPLE 15

Synthesis of 5'-O-DMTr-T-T-3'-O-DMTr-phosphorothioate diester

To a solution of 5'-O-DMTr-T-T-3'-O-DMTr H-phosphonate diester (25 mg, 22 mmol) in dichloromethane is added AMBERLYST A26 tetrathionate form (170 mg, 0.29 mmol $S_4O_6^{2-}$, 13 eq.) and 0.1 mL triethylamine. The reaction mixture is shaken for 78 h. The title compound was isolated after filtration of the resin and evaporation of the solvent. Yield: 28 mg, 22 mmol, 100%; $^{31}$P NMR (CD$_3$CN) d 57.22; MALDI-TOF MS (negative mode, trihydroxy-acetophenone as matrix) [M−H]− m/z$_{exp}$=1166.23, m/z$_{calc}$=1666.25.

EXAMPLE 16

Synthesis of 5'-O-DMTr-T-T-3'-O-TBDMS-phosphorothioate diester

To a solution of 5'-O-DMTr-T-T-3'-O-TBDMS H-phosphonate (55 mg, 58 mmol) in dichioromethane is added AMBERLYST A26 tetrathionate form (250 mg, 0.42 mmol $S_4O_6^{2-}$, 7.3 eq.) and 0.2 mL triethylamine. The reaction mixture is shaken for 26 h. The title compound was isolated after filtration of the resin and evaporation of the solvent. Yield: 63 mg, 58 mmol, 100%; $^{31}$P NMR (CD$_3$CN) δ 57.78, 57.72; MALDI-TOF MS (negative mode, trihydroxyacetophenone as matrix) [M−H]− m/z$_{exp}$=977.04, m/z$_{calc}$=977.13.

EXAMPLE 17

Synthesis of AMBERLYST A26 tetrathionate form 10 g commercial Amberiyst A26 hydroxide form (Rohm & Haas) is washed twice with 20 mL methanol and twice with 20 mL dichloromethane and dried in vacuum. Potassium tetrathionate (30.35 g, 100 mmol, 3 eq.) is dissolved in 200 mL deionized water. The solution is added to the resin and shaken for 20 hours. The solution is decanted of. The resin is washed with 4 L deionized water, twice with 100 mL methanol and twice with 100 mL dichloromethane and dried under reduced pressure for 3 hours to give 8.5 g of solid-supported tetrathionate. The reagents loading was determined by elemental analysis, giving a value of 23.25% for sulfur (4.24% for nitrogen, 45.74% for carbon and less than 100 ppm for potassium). Loading: 1.81 mmol $S_4O_6^{2-}$ per gram of resin.

EXAMPLE 18

Synthesis of polymer-supported pyridinium

The commercially available strongly acidic ion-exchange resin DOWEX 50W X8 H+ form (Fluke) is washed successively with water, HCl 2M, water until pH 7, methanol and dichloromethane to dry the resin. Then, the resin is stirred in a solution of pyridine 2M in acetonitrile or just washed with a slight flow of the solution of pyridine 2M in acetonitrile for 15 minutes. Then, the resin is washed with acetonitrile and dichloromethane and dried under vacuum over $P_2O_5$. The reagents loading was determined by elemental analysis, giving a value of 11.56% for sulfur and 3.97% for nitrogen. Loading: 2.83 mmol pyrH+ per gram of resin.

EXAMPLE 19

Preparation of polystyrene-bound acid chloride

The commercial polystyrene-bound carboxy acid RAPP Polymere (5.0 g, 1.96 mmol/g, 100-200 mesh, 1% DVB) is suspended in anhydrous CH$_2$Cl$_2$ (80 ml) and N,N-dimethylformamide (0.3 ml). Thionyl chloride (1.8 ml, 3.5 eq) are added under stirring and the mixture is refluxed for 3 h. The resin is filtered under argon and washed with dried CH$_2$Cl$_2$ (100 ml), ether (100 ml) and dried under vacuum for 4 h.

IR (cm$^{-1}$): 1775 (C=O, Acid chloride)

Elemental analysis: Cl 7.43% (w/100 g resin) (2.09 mmol/g)

Chloride titration: 2.1 mmol/g

EXAMPLE 20

Synthesis of 5'-O-DMTr-dA$^{Bz}$-dC$^{Bz}$-3'-O-Lev H-phosphonate

A solution of 5'-O-DMTr-dA$^{Bz}$-H-phosphonate TEA salt (123.4 mg, 0.150 mmol) and of 3'-O-Lev-dC$^{Bz}$ (53.7 mg, 0.125 mmol) in 2.0 ml of CH$_2$Cl$_2$/py (1:1) is added to polystyrene-bound acid chloride (388.8 mg, 2.1 mmol/g, 5.5 eq) that is suspended in 2.5 ml of the same solvent. The mixture is shaken for 1 h at room temperature until the disappearance of the monomers. The reaction is monitored by reverse phase HPLC. The resin is filtered, washed with CH$_2$Cl. The pyridinium salt present in solution is removed by aqueous extraction and the aqueous phase is washed twice with CH$_2$Cl$_2$. The organic fractions are collected, dried over Na$_2$SO$_4$, the solvent is evaporated and the pyridine is eliminated by coevaporation with toluene. The isolated product was dried under vacuum. Yield 89%.

$^{31}$P NMR (CD$_3$CN) δ 10.03 ppm, 9.46 ppm.

MALDI-TOF MS (positive mode, trihydroxyacetophenone as matrix) [M+H]+ m/z$_{exp}$=1134.13, m/z$_{calc}$=1133.51.

The spectrophotometrical purity determined by HPLC is 93%.

EXAMPLE 21

Synthesis of 5'-O-DMTr-dA$^{Bz}$-T-3'-O-Lev H-phosphonate

A solution of 5'-O-DMTr-dA$^{Bz}$-H-phosphonate TEA salt (123.4 mg, 0.150 mmol) and of 3'-O-Lev-T (42.5 mg, 0.125 mmol) in 2.0 ml of CH$_2$Cl/py (1:1) is added to polystyrene-bound acid chloride (550.0 mg, 2.1 mmol/g, 7.7 eq) that is suspended in 5.0 ml of the same solvent. The mixture is shaken for 30 min at room temperature until the disappearance of the monomers. The reaction is monitored by reverse phase HPLC. The resin is filtered, washed with CH$_2$Cl. The pyridinium salt present in solution is removed by aqueous extraction and the aqueous phase is washed twice with CH$_2$Cl. The organic fractions are collected, dried over Na$_2$SO$_4$, the solvent is evaporated and the pyridine is eliminated by coevaporation with toluene. The isolated product is dried under vacuum. Yield 88.5%

$^{31}$P NMR (CD$_3$CN) δ 10.02 ppm, 9.08 ppm.

MALDI-TOF MS (positive mode, trihydroxyacetophenone as matrix) [M−H]+ m/z$_{exp}$=1043.02, m/z$_{calc}$=1045.00.

The spectrophotometrical purity determined by HPLC is 98%.

EXAMPLE 22

Synthesis of 5'-O-DMTr-T-dC$^{Bz}$-3'-O-TBDMS H-phosphonate

A solution of 5'-O-DMTr-T-H-phosphonate TEA salt (106.4 mg, 0.150 mmol) and of 3'-O-TBDMS-dC$^{Bz}$ (55.7 mg, 0.125 mmol) in 2.0 ml of CH$_2$Cl/py (1:1) is added to polystyrene-bound acid chloride (555.0 mg, 2.7 mmol/g, 10 eq) that is suspended in 5.0 ml of the same solvent. The mixture is shaken for 2 h at room temperature until the disappearance of the monomers. The reaction is monitored by reverse phase HPLC. The resin is filtered, washed with CH$_2$Cl$_2$. The pyridinium salt present in solution is removed by aqueous extraction and the aqueous phase is washed twice with CH$_2$Cl$_2$. The organic fractions are collected, dried over Na$_2$SO$_4$, the solvent is evaporated and the pyridine is eliminated by coevaporation with toluene. The isolated product is dried under vacuum. Yield 77.5%.

$^{31}$P NMR (CD$_3$CN) δ 10.50 ppm, 10.00 ppm.

MALDI-TOF MS (positive mode, trihydroxyacetophenone as matrix) [M+H]$^+$ m/z$_{exp}$=1038.69, m/z$_{calc}$=1037.20.

The spectrophotometrical purity determined by HPLC is 94%.

EXAMPLE 23

Synthesis of 5'-O-DMTr-T-dC$^{Bz}$-3'-O-TBDMS phosphorothioate TEA salt

A solution of 5'-O-DMTr-T-dC$^{Bz}$-3'-O-TBDMS H-phosphonate (50 mg, 0.048 mmol) in 5.0 ml of CH$_2$Cl$_2$ and 0.2 ml TEA is added to Amberlyst A26 tetra-thionate form (141.0 mg, 1.7 mmol/g, 5 eq). The mixture is shaken over night, the the resin is filtered and the solvent is evaporated. The product is dried under vacuum. Yield 100%.

$^{31}$P NMR (CD$_2$Cl$_2$) δ 59.17 ppm, 58.99 ppm.

The spectrophotometrical purity determined by HPLC is 95%.

EXAMPLE 24

Synthesis of 5'-O-DMTr-dA$^{Bz}$-T-3'-O-Lev phosphate TEA salt

A solution of 5'-O-DMTr-dA$^{Bz}$-T-3'-O-Lev H-phosphonate (90 mg, 0.0863 mmol) in 5.0 ml of CH$_2$Cl$_2$ and 0.2 ml TEA is added to (polystyrilmethyl)trimethylamonium metaperiodate (NOVABIOCHEM) (173.0 mg, 2.5 mmol/g, 5 eq). The mixture is shaken over night, the resin is filtered and the solvent is evaporated. The product is dried under vacuum. Yield 100%.

$^{31}$P NMR (CD$_2$Cl$_2$) δ −1.37 ppm.

MALDI-TOF MS (positive mode, trihydroxyacetophenone as matrix) [M+H]$^+$ m/z$_{exp}$=1059.31, m/z$_{calc}$=1060.03.

The spectrophotometrical purity determined by HPLC is 87%.

EXAMPLE 25

Synthesis of 5'-O-DMTr-T-dA$^{Bz}$-dC$^{Bz}$-3'-O-Lev H-phosphonate

Detritylation of 5'-O-DMTr-dA$^{Bz}$-dC$^{Bz}$-3'-O-Lev H-phosphonate

The H-phosphonate dimer 5'-O-DMTr-dA$^{Bz}$-dC$^{Bz}$-3'-O-Lev (120 mg, 0.106 mmol) is dissolved in 4.0 ml of CH$_2$Cl$_2$/MeOH (7:3) and cooled in an ice bath. To this solution 1.0 ml of a solution of 10% BSA (benzene sulfonic acid) in CH$_2$Cl/MeOH (7:3) is added drop wise under stirring and the progress of the reaction is monitored by TLC. After 15 min the mixture is quenched with a solution of NaHCO$_3$. The organic layer is washed with water to remove any trace of base, then it is dried over Na$_2$SO$_4$ and the solvent is evaporated. The product is purified by precipitation from CH$_2$Cl$_2$ with ether and dried under vacuum. Yield 88%, MALDI-TOF MS (positive mode, trihydroxyacetophenone as matrix) [M+H]$^+$ m/z$_{exp}$=830.75, m/z$_{calc}$=831.75.

The spectrophotometrical purity determined by HPLC is 91%.

Coupling

A solution of 5'-O-DMTr-T-H-phosphonate TEA salt (93.8 mg, 0.132 mmol) and of 5'-OH-dA$^{Bz}$-dC$^{Bz}$-3'-O-Lev H-phosphonate (73.2 mg, 0.088 mmol) in 2.0 ml of CH$_2$Cl$_2$/py (1:1) is added to polystyrene-bound acid chloride (503.0 mg, 2.1 mmol/g, 8 eq) that is suspended in 4.0 ml of the same solvent, The mixture is shaken for 1 h at room temperature until the disappearance of the monomers. The reaction is monitored by reverse phase HPLC. The resin is filtered, washed with CH$_2$Cl$_2$. The pyridinium salt present in solution is removed by aqueous extraction and the aqueous phase is washed twice with CH$_2$Cl$_2$, The organic fractions are collected, dried over Na$_2$SO$_4$, the solvent is evaporated and the pyridine is eliminated by coevaporation with toluene. The isolated product is dried under vacuum, Yield 82%.

$^{31}$P NMR (CD$_2$Cl$_2$) δ 10.23, 10.09, 9.70, 9.68, 9.52, 9.30, 9.24, 9.19 ppm.

MALDI-TOF MS (positive mode, trihydroxyacetophenone as matrix) [M+H]$^+$ m/z$_{exp}$=1421.06, m/z$_{calc}$=1422.33.

The spectrophotometrical purity determined by HPLC is 82%.

EXAMPLE 26

Synthesis of 5'-O-DMTr-dA$^{Bz}$-dA$^{Bz}$-T-3'-O-Lev H-phosphonate

Detritylation of 5'-O-DMTr-de-T-3'-O-Lev H-phosphonate

The H-phosphonate dimer 5'-O-DMTr-dA$^{Bz}$-T-3'-O-Lev (105 mg, 0.100 mmol) is dissolved in 4.0 ml of CH$_2$Cl/MeOH (7:3) and cooled in an ice bath. 1.0 ml of a solution of 10% BSA in CH$_2$Cl$_2$/MeOH (7:3) is added drop wise under stirring and the progress of the reaction is monitored by TLC. After 15 min the mixture is quenched with a solution of NaHCO$_3$. The organic layer is washed with water to remove any trace of base, then it is dried over Na$_2$SO$_4$ and the solvent is evaporated. The product is purified by precipitation from CH$_2$Cl$_2$ in ether and dried under vacuum. Yield 70%.

MALDI-TOF MS (positive mode, trihydroxyacetophenone as matrix) [M+H]$^+$ m/z$_{exp}$=742.25, m/z$_{calc}$=742.66.

The spectrophotometrical purity determined by HPLC is 92%.

Coupling

A solution of 5'-O-DMTr-dA$^{Bz}$-H-phosphonate TEA salt (69.8 mg, 0.084 mmol) and of 5'-OH-dA$^{Bz}$-dT-3'-O-Lev H-phosphonate (52.2 mg, 0.070 mmol) in 2.0 ml of CH$_2$Cl$_2$/py (1:1) is added to polystyrene-bound acid chloride (311.0 mg, 2.1 mmol/g, 7.7 eq) that is suspended in 2.0 ml of the same solvent. The mixture is shaken for 3 h at room temperature until the disappearance of the monomers. The reaction is monitored by reverse phase HPLC. The resin is filtered, washed with CH$_2$Cl$_2$. The pyridinium salt present in solution is removed by aqueous extraction and the aqueous phase is washed twice with CH$_2$Cl$_2$. The organic fractions are collected, dried over Na$_2$SO$_4$, the solvent is evaporated and the pyridine is eliminated by coevaporation with toluene. The isolated product is dried under vacuum. Yield 75%.

$^{31}$P NMR (CD$_2$Cl$_2$) δ 10.09, 9.39, 8.82, 8.76, 8.30, 7.56 ppm.

MALDI-TOF MS (positive mode, trihydroxyacetophenone as matrix) [M+]$^+$ m/z$_{exp}$=1445.60, m/z$_{calc}$=1447.40.

The spectrophotometrical purity determined by HPLC is 91.5%.

EXAMPLE 27

Synthesis of the Dimer 5'-OH-T-dG$^{IBu}$-3'-O-Lev Cyanoethyl Phosphorothioate Triester Coupling procedure of 5'-O-DMTr-T-3'-cyanoethyl-phosphoramidite with 5'-OH-dG$^{IBu}$-3'-O-Lev using the poly(4-vinylpyridinum p-toluenesulfonate) (Aldrich):

5'-OH-dG$^{IBu}$-3'-O-Lev (201 mg, 0.46 mmol) and 5'-O-DMTr-T-3'-cyanoethyl-phosphoramidite (620 mg, 0.83 mmol, 1.8 eq) are dissolved in anhydrous dichloromethane (10 ml). The solution is transferred under argon in a flask containing the poly(4-vinylpyridinum p-toluenesulfonate) (1.38 g, 4.6 mmol tos$^-$, 10 eq) and is shaken for 3 h. The resin is filtered off. The reaction is followed by reverse phase HPLC and $^{31}$P NMR. The yield is determined by $^{31}$P NMR. The desired T-dG phosphite triester dimer is obtained with 100% of yield compared to the 5'-OH-dG$^{IBu}$-3'-O-Lev. The crude is a mixture of 5'-O-DMTr-T-dG$^{IBu}$-3'-O-Lev cyanoethyl phosphite triester $^{31}$P NMR (CDCl$_3$) (d 140.76, 139.97; 60.7%) and 5'-O-DMTr-T-3'-cyanoethyl hydrogenophosphonate (d 8.10, 8.03; 39.3%).

Sulfurization: To a solution of 5'-O-DMTr-T-dG$^{IBu}$-3'-O-Lev cyanoethyl phosphite triester dimer (0.46 mmol) in anhydrous dichloromethane is added AMBERLYST A26 tetrathionate form (1.28 g, 2.3 mmol S$_4$O$_6^{2-}$, 5 eq.). The reaction mixture is shaken for 2 h. The reaction is followed by reverse phase HPLC and $^{31}$P NMR. The yield is determined by $^{31}$P NMR. After filtration of the resin the desired T-dG phosphorothioate triester dimer is obtained with 100% of yield compared to the 5'-OH-dG$^{IBu}$-3'-O-Lev. The crude is a mixture of 5'-O-DMTr-T-dG$^{IBu}$-3'-O-Lev cyanoethyl phosphorothioate $^{31}$P NMR (CDCl$_3$) (d 67.99, 67.71; 64.7%) and 5'-O-DMTr-T-3'-cyanoethyl hydrogenophosphonate (d 8.09, 8.02; 35.3%); MALDI-TOF MS (positive mode, trihydroxyacetophenone as matrix) [M-DMTr]$^+$ m/z$_{exp}$=809.00, m/z$_{calc}$=809.77.

Detritylation: To a solution of 5'-O-DMTr-T-dG$^{IBu}$-3'-O-Lev cyanoethyl phosphorothioate triester (0.46 mmol) in 20 ml CH$_2$Cl/CH$_3$OH (7/3) is added 2 ml (1.2 mmol, 1.4 eq.) of a solution of benzene sulfonic acid 10% in CH$_2$Cl$_2$/CH$_3$OH (7/3). The solution is stirred 25 min at 0° C. The reaction is is washed with 10 ml of a saturated solution of NaHCO$_3$, the organic layer is separated, dried (MgSO$_4$) and evaporated. The crude product is dissolved in 3.5 mL dichloromethane and added to 50 mL diethylether at 0° C. to give a white precipitate. Yield: 370 mg, 0.46 mmol, 99%; $^{31}$P NMR (CDCl$_3$) d 67.77, 67.42; MALDI-TOF MS (positive mode, trihydroxyacetophenone as matrix) [M-H]$^+$ m/z$_{exp}$=910.42, m/z$_{calc}$=909.77; HPLC HPLC (7.27 min; Area=85%).

EXAMPLE 28

Synthesis of the dimer 5'-OH-dA$^{Bz}$-dG$^{IBu}$-3'-O-Lev Cyanoethyl Phosphorothioate Triester Coupling procedure of 5-'-O-DMTr-dA$^{Bz}$-3'-cyanoethyl-phosphoramidite with 5'-OH-dG$^{IBu}$-3'-O-Lev using the poly (4-vinylpyridinum p-toluenesulfonate) (Aldrich):

5'-OH-dG$^{IBu}$-3'-O-Lev (200 mg, 0.46 mmol) and 5'-O-DMTr-dA$^{Bz}$-3'-cyanoethyl-phosphoramidite (713 mg, 0.83 mmol, 1.8 eq) are dissolved in anhydrous dichloromethane (10 ml). The solution is transferred under argon in a flask containing the poly(4-vinylpyridinum p-toluenesulfonate) (1.38 g, 4.6 mmol tos$^-$, 10 eq) and is shaken for 2 h. The resin is filtered off. The reaction is followed by reverse phase HPLC and $^{31}$P NMR. The yield is determined by HPLC. The desired dA$^{Bz}$-dG phosphite triester dimer (HPLC at 11.34 min; Area=61%) is obtained with 100% of yield compared to the 5'-OH-dG$^{IBu}$-3'-O-Lev (HPLC at 6.34 min; Area=0%). The crude is a mixture of 5'-O-DMTr-dA$^{Bz}$-dG$^{IBu}$-3'-O-Lev cyanoethyl phosphite triester $^{31}$P NMR (CDCl$_3$) (d 140.82, 140.30), 5'-O-DMTr-dA$^{Bz}$-3'-cyanoethyl phosphoramidite (d 149.90) and 5'-O-DMTr-dA$^{Bz}$-3'-cyanoethyl hydrogenophosphonate (d 8.20, 8.03).

Sulfurization: To a solution of 5'-O-DMTr-dA$^{Bz}$-dG$^{IBu}$-3'-O-Lev cyanoethyl phosphite triester dimer (0.46 mmol) in anhydrous dichloromethane is added AMBERLYST A26 tetrathionate form (1.28 g, 2.3 mmol S$_4$O$_6^{2-}$, 5 eq.). The reaction mixture is shaken for 2 h. The reaction is followed by reverse phase HPLC and $^{31}$P NMR. The yield is determined by HPLC. After filtration of the resin the desired dA$^{Bz}$-dG phosphorothioate triester dimer (HPLC at 11.49 min; Area=61%) is obtained with 100% of yield compared to the 5'-OH-dG$^{IBu}$-3'-O-Lev. The crude is a mixture of 5'-O-DMTr-dA$^{Bz}$-dG$^{IBu}$-3'-O-Lev cyanoethyl phosphorothioate $^{31}$P NMR (CDCl$_3$) (d 68.01, 67.93), 5'-O-DMTr-dA$^{Bz}$-3'-cyanoethyl thiophosphoramidate (d 71.86, 71.54) and 5'-O-DMTr-dA$^{Bz}$-3'-cyanoethyl hydrogenophosphonate (d 8.20, 8.03); MALDI-TOF MS (positive mode, trihydroxyacetophenone as matrix) [M-H]$^+$ m/z$_{exp}$=1224.14, m/z$_{calc}$=1225.27.

Detritylation: To a solution of 5'-O-DMTr-dA$^{Bz}$-dG$^{IBu}$-3'-O-Lev cyanoethyl phosphorothioate triester (0.46 mmol) in 20 ml CH$_2$Cl$_2$/CH$_3$OH (7/3) is added 2 ml (1.2 mmol, 1.4 eq.) of a solution of benzene sulfonic acid 10% in CH$_2$Cl$_2$/CH$_3$OH (7/3), The solution is stirred 20 min at 0° C. Another 1 ml (0.6 mmol, 0.7 eq.) of a solution of benzene sulfonic acid 10% in CH$_2$Cl/CH$_3$OH (7/3) is added and the solution is stirred for 40 min. The reaction is washed with 10 ml of a saturated solution of NaHCO$_3$, the organic layer is separated, dried (MgSO$_4$) and evaporated. The crude product is dissolved in 4 mL dichloromethane and added to 50 mL diethylether at 0° C. to give a white precipitate. Yield: 442 mg, 0.4 mmol, 87%; $^{31}$P NMR (CDCl$_3$) d 68.09, 67.78; MALDI-TOF MS (positive mode, trihydroxyacetophenone as matrix) [M-H]$^+$ m/z$_{exp}$=923.03, m/z$_{calc}$=922.89; HPLC (8.08 min; Area=85%).

EXAMPLE 29

Synthesis of the Dimer 5'-Oh-dC$^{Bz}$-dG$^{iBu}$-3'-O-Lev Cyanoethyl Phosphorothioate Triester Coupling procedure of 5'-O-DMTr-dC$^{Bz}$-3'-cyanoethyl-phosphoramidite with 5'-OH-dG$^{iBu}$-3'-O-Lev using the poly (4-vinylpyridinum p-toluenesulfonate) (Aldrich):

5'-OH-dG$^{iBu}$-3'-O-Lev (200 mg, 0.46 mmol) and 5'-O-DMTr-dC$^{Bz}$-3'-cyanoethyl-phosphoramidite (694 mg, 0.83 mmol, 1.8 eq) are dissolved in anhydrous dichloromethane (10 ml), The solution is transferred under argon in a flask containing the poly(4-vinylpyridinum p-toluenesulfonate) (1.38 g, 4.6 mmol tos⁻, 10 eq) and is shaken for 3 h. The resin is filtered off. The reaction is followed by reverse phase HPLC and $^{31}$P NMR. The yield is determined by HPLC. The desired dC-dG phosphite triester dimer (HPLC at 12.01 min; Area=50%) is obtained with 100% of yield compared to the 5'-OH-dG$^{iBu}$-3'-O-Lev (HPLC at 6.34 min; Area=0%). The crude is a mixture of 5'-O-DMTr-dC$^{Bz}$-dG$^{iBu}$-3'-O-Lev cyanoethyl phosphite triester $^{31}$P NMR (CDCl$_3$) (d 140.67, 140.59), 5'-O-DMTr-dC$^{Bz}$-3'-cyanoethyl phosphoramidite (d 149.93) and 5'-O-DMTr-dC$^{Bz}$-3'-cyanoethyl hydrogeno-phosphonate (d 8.08).

Sulfurization: To a solution of 5'-O-DMTr-dC$^{Bz}$-dG$^{iBu}$-3'-O-Lev cyanoethyl phosphite triester dimer (0.46 mmol) in anhydrous dichloromethane is added AMERLYST A26 tetrathionate form (1.37 g, 2.5 mmol S$_4$O$_6^{2-}$, 5.4 eq.). The reaction mixture is shaken for 3 h. The reaction is followed by reverse phase HPLC and $^{31}$P NMR. The yield is determined by HPLC. After filtration of the is resin the desired dC-dG phosphorothioate triester dimer (HPLC at 12.26 min; Area=59%) is obtained with 100% of yield compared to the 5'-OH-dG$^{iBu}$-3'-O-Lev. The crude is a mixture of 5'-O-DMTr-dC$^{Bz}$-dG$^{iBu}$-3'-O-Lev cyanoethyl phosphorothioate $^{31}$P NMR (CDCl$_3$) (d 68.02, 67.55), 5'-O-DMTr-dC$^{Bz}$-3'-cyanoethyl thiophosphoramidate (d 71.93, 71.62) and 5'-O-DMTr-dC$^{Bz}$-3'-cyanoethyl hydrogeno-phosphonate (d 8.07).

Detritylation: To a solution of 5'-O-DMTr-dC$^{Bz}$-dG$^{iBu}$-3'-O-Lev cyanoethyl phosphorothioate triester (0.46 mmol) in 20 ml CH$_2$Cl$_2$/CH$_3$OH (7/3) is added 2 ml (1.2 mmol, 1.4 eq.) of a solution of benzene sulfonic acid 10% in CH$_2$Cl$_2$/CH$_3$OH (7/3). The solution is stirred 20 min at 0° C. Another 1 ml (0.6 mmol, 0.7 eq.) of a solution of benzene sulfonic acid 10% in CH$_2$Cl$_2$/CH$_3$OH (7/3) is added and the solution is stirred for 10 min. The reaction is washed with 10 ml of a saturated solution of NaHCO$_3$, the organic layer is separated, dried (MgSO$_4$) and evaporated. The crude product is dissolved in 7 mL dichloromethane and added to 50 mL. diethylether at 0° C. to give a white precipitate. Yield: 493 mg, 0.33 mmol, 71%; $^{31}$P NMR (CDCl$_3$) d 67.38, 66.77; MALDI-TOF MS (positive mode, trihydroxyacetophenone as matrix) [M−H]$^+$ m/z$_{exp}$=898.84, m/z$_{calc}$=898.86; HPLC (8.34 min; Area=60%).

EXAMPLE 30

Synthesis of the dimer 5'-OH-dG$^{iBu}$-dG$^{iBu}$-3'-O-Lev Cyanoethyl Phosphorothioate Triester Coupling procedure of 5'-O-DMTr-dG$^{iBu}$-3'-cyanoethyl-phosphoramidite with 5'-OH-OG$^{iBu}$-3'-O-Lev using the poly (4-vinylpyridinum p-toluenesulfonate) (Aldrich):

5'-OH-dG$^{iBu}$-3'-O-Lev (200 mg, 0.46 mmol) and 5'-O-DMTr-dG$^{iBu}$-3'-cyanoethyl-phosphoramidite (698 mg, 0.84 mmol, 1.8 eq) are dissolved in anhydrous dichloromethane (10 ml). The solution is transferred under argon in a flask containing the poly(4-vinylpyridinum p-toluenesulfonate) (1.38 g, 4.6 mmol tos⁻, 10 eq) and is shaken for 1 h 15 min. The resin is filtered off. The reaction is followed by reverse phase HPLC and $^{31}$P NMR. The yield is determined by HPLC. The desired dG-dG phosphite triester dimer (HPLC at 11.01 min; Area=65%) is obtained with 100% of yield compared to the 5'-OH-dG$^{iBu}$-3'-O-Lev (HPLC at 6.34 min; Area=0%). The crude is a mixture of 5'-O-DMTr-dG$^{iBu}$-dG$^{iBu}$-3'-O-Lev cyanoethyl phosphite triester $^{31}$P NMR (CDCl$_3$) (d 141.91, 140.29) and 5'-O-DMTr-dG$^{iBu}$-3'-cyanoethyl hydrogenophosphonate (d 8.80, 8.06).

Sulfurization: To a solution of 5'-O-DMTr-dG$^{iBu}$-dG$^{iBu}$-3'-O-Lev cyanoethyl phosphite triester dimer (0.46 mmol) in anhydrous dichloromethane is added AMBERLYST A26 tetrathionate form (1.28 g, 2.3 mmol S$_4$O$_6^{2-}$, 5 eq.). The reaction mixture is shaken for 1 h 20 min. The reaction is followed by reverse phase HPLC and $^{31}$P NMR. The yield is determined by HPLC. After filtration of the resin the desired dG-dG phosphorothioate triester dimer (HPLC at 11.52 min; Area=75%) is obtained with 100% of yield compared to the 5'-OH-dG$^{iBu}$-3'-O-Lev. The crude is a mixture of 5'-O-DMTr-dG$^{iBu}$-dG$^{iBu}$-3'-O-Lev cyanoethyl phosphorothioate $^{31}$P NMR (CDCl$_3$) (d 68.61, 67.64) and 5'-O-DMTr-dG$^{iBu}$-3'-cyanoethyl hydrogenophosphonate (d 8.07); MALDI-TOF MS (positive mode, trihydroxyacetophenone as matrix) [M−DMTr]$^+$ m/z$_{exp}$=904.14, m/z$_{calc}$=904.87.

Detritylation: To a solution of 5'-O-DMTr-dG$^{iBu}$-dG$^{iBu}$-3'-O-Lev cyanoethyl phosphorothioate triester (0.46 mmol) in 20 ml CH$_2$Cl$_2$/CH$_3$OH (7/3) is added 2 ml (1.2 mmol, 1.4 eq.) of a solution of benzene sulfonic acid 10% in CH$_2$Cl$_2$/CH$_3$OH (7/3). The solution is stirred 25 min at 0° C. The reaction is washed with 10 ml of a saturated solution of NaHCO$_3$, the organic layer is separated, dried (MgSO$_4$) and evaporated. The crude product is dissolved in 7.5 mL dichloromethane and added to 50 mL diethylether at 0° C. to give a white precipitate. Yield: 450 mg, 0.41 mmol, 88; $^{31}$P NMR (CDCl$_3$) d 67.85, 67.66; MALDI-TOF MS (positive mode, trihydroxyacetophenone as matrix) [M−H]$^+$ m/z$_{exp}$=905.45, m/z$_{calc}$=904.87; HPLC (7.95 min; Area=82%).

EXAMPLE 31

Synthesis of the Trimer Cyanoethyl Phosphorothioate Triester

Coupling procedure of 5'-O-DMTr-dA$^{Bz}$-3'-cyanoethyl-phosphoramidite with 5'-OH-T-dG$^{iBu}$-3'-O-Lev cyanoethyl phosphorothioate triester using the poly(4-vinylpyridinum p-toluenesulfonate) (Aldrich):

5'-OH-T-dG$^{iBu}$-3'-O-Lev cyanoethyl phosphorothioate triester (362 mg, 0.4 mmol) and 5'-O-DMTr-dA$^{Bz}$-3'-cyanoethyl-phosphoramidite (623 mg, 0.73 mmol, 1.8 eq) are dissolved in anhydrous dichloromethane (15 ml). The solution is transferred under argon in a flask containing the poly(4-vinylpyridinum p-toluenesulfonate) (1.2 g, 4.0 mmol tos⁻, 10 eq) and is shaken for 6 h 20 min. Water (50 mL) is added to hydrolyze the remaining phosphoramidite. After 1 h the resin is filtered off. The reaction is followed by reverse phase HPLC and $^{31}$P NMR. The yield is determined by HPLC. The desired dA-T-dG is phosphite triester trimer (HPLC at 11.32 min; Area=66%) is obtained with 100% of yield compared to the 5'-OH-T-dG$^{iBu}$-3'-O-Lev cyanoethyl phosphorothioate triester (HPLC at 7.27 min; Area=0%). The crude is a mixture of 5'-O-DMTr-dA$^{Bz}$-3'-cyanoethyl-phosphite-T-3'-cyanoethyl-thionophosphotriester-dG$^{iBu}$-3'-O-Lev trimer $^{31}$P NMR (CDCl$_3$) (d 140.97, 140.79, 140.40, 139.90, 67.89, 67.87, 67.83) and 5'-O-DMTr-dA$^{Bz}$-3'-cyanoethyl hydrogenophosphonate (d 8.12, 8.03).

Sulfurization: To a solution of 5'-O-DMTr-dA$^{Bz}$-3'-cyanoethyl-phosphite-T-3'-cyanoethyl-thionophosphotriester-dG$^{IBu}$-3'-O-Lev (0.4 mmol) in anhydrous dichloromethane is added AMBERLYST A26 tetrathionate form (1.12 g, 2.0 mmol S$_4$O$_6^{2-}$, 5 eq.). The reaction mixture is shaken for 14 h. The reaction is followed by reverse phase HPLC and $^{31}$P NMR. The yield is determined by HPLC. After filtration of the resin the desired dA-T-dG phosphorothioate triester trimer (HPLC at 11.63 min; Area=64%) is obtained with 100% of yield compared to the 5'-OH-T-dG$^{IBu}$-3'-O-Lev cyanoethyl phosphorothioate triester. The crude is a mixture of 5'-O-DMTr-dA$^{Bz}$-T-dG$^{IBu}$-3'-O-Lev cyanoethyl phosphorothioate triester $^{31}$P NMR (CDCl$_3$) (d 68.05, 67.92, 67.84, 67.68) and 5'-O-DMTr-dA$^{Bz}$-3'-cyanoethyl hydrogenophosphonate (d 8.16, 7.98); MALDI-TOF MS (positive mode, trihydroxyacetophenone as matrix) [M-DMTr]$^+$ m/z$_{exp}$=1583.16, m/z$_{calc}$=1582.53.

Detritylation: To a solution of 5'O-DMTr-dA$^{Bz}$-T-dG$^{IBu}$-3'-O-Lev cyanoethyl phosphorothioate triester (0.4 mmol) in 60 ml CH$_2$Cl$_2$/CH$_3$OH (7/3) is added 4 ml (2.5 mmol, 6.3 eq.) of a solution of benzene sulfonic acid 10% in CH$_2$Cl$_2$/CH$_3$OH (7/3). The solution is stirred 30 min at 0° C. The reaction is washed with 10 ml of a saturated solution of NaHCO$_3$, the organic layer is separated, dried (MgSO$_4$) and evaporated. The crude product is dissolved in 10 mL dichloromethane and added to 50 mL. diethylether at 0° C. to give a white precipitate. Yield: 543 mg, 0.32 mmol, 80%; $^{31}$P NMR (CDCl$_3$) d 67.94, 67.79, 67.72, 67.66, 67.58, 67.28, 67.14; MALDI-TOF MS (positive mode, trihydroxyacetophenone as matrix) [M-H]$^+$ m/z$_{exp}$=1296.07, m/z$_{calc}$=1296.22; HPLC (9.39 min; Area=77%).

EXAMPLE 32

Synthesis of the Tetramer 5'-OH-dC$^{Bz}$-dG$^{IBu}$-T-T-3'-O-Lev Cyanoethyl Phosphorothioate Triester 1$^{st}$ Coupling procedure of 5'-O-DMTr-T-3'-cyanoethyl-phosphoramidite with 5'-OH-T-3'-O-Lev using the poly(4-vinylpyridinum p-toluenesulfonate) (Aldrich) providing the 5'O-DMTr-T-T-3'-O-Lev cyanoethyl phosphite triester dimer:

5'-OH-T-3'-O-Lev (340 mg, 1.0 mmol) and 5'-O-DMTr-T-3'-cyanoethyl-phosphoramidite (1266 mg, 1.7 mmol, 1.7 eq) are dissolved in anhydrous dichloromethane (10 ml). The solution is transferred under argon in a flask containing the poly(4-vinylpyridinum p-toluenesulfonate) (3.0 g, 10 mmol tos$^-$, 10 eq) and is shaken for 5 h 15 min. Water (50 mL) is added to hydrolyze the remaining phosphoramidite. After 1 h 15 min the resin is filtered off. The reaction is followed by reverse phase HPLC and $^{31}$P NMR. The yield is determined by HPLC. The desired T-T phosphite triester dimer (HPLC at 11.14 min; Area=71%) is obtained with 100% of yield compared to the 5'-OH-T-3'-O-Lev (HPLC at 5.49 min; Area=0%). The crude is a mixture of 5'-O-DMTr-T-T-3'-O-Lev cyanoethyl phosphite triester $^{31}$P NMR (CDCl$_3$) (d 140.58, 140.31) and 5'-O-DMTr-T-3'-cyanoethyl hydrogenophosphonate (d 8.10, 8.04).

1st Sulfurization: To a solution of 5'-O-DMTr-T-T-3'-O-Lev cyanoethyl phosphite triester dimer (1.0 mmol) in anhydrous dichloromethane is added AMBERLYST A26 tetrathionate form (3.89 g, 7.0 mmol S$_4$O$_6^{2-}$, 7 eq.). The reaction mixture is shaken for 20 h. The reaction is followed by reverse phase HPLC and $^{31}$P NMR. The yield is determined by HPLC. After filtration of the resin the desired T-T phosphorothioate triester dimer (HPLC at 11.44 min; Area=75%) is obtained with 100% of yield compared to the 5'-OH-T-3'-O-Lev. The crude is a mixture of 5'-O-DMTr-T-T-3'-O-Lev cyanoethyl phosphorothioate $^{31}$P NMR (CDCl$_3$) (d 68.20, 68.14) and 5'-O-DMTr-T-3'-cyanoethyl hydrogenophosphonate (d 8.11, 8.05).

Detritylation: To a solution of 5'-O-DMTr-T-T-3'-O-Lev cyanoethyl phosphorothioate triester (1.0 mmol) in 70 ml CH$_2$Cl$_2$/CH$_3$OH (7/3) is added 4 ml (2.5 mmol, 2.5 eq.) of a solution of benzene sulfonic acid 10% in CH$_2$Cl$_2$/CH$_3$OH (7/3). The solution is stirred 40 min at 0° C. The reaction is washed with 10 ml of a saturated solution of NaHCO$_3$, the organic layer is separated, dried (MgSO$_4$) and evaporated. The crude product is dissolved in 8 mL dichloromethane and added to 50 mL diethylether at 0° C. to give a white precipitate. Yield: 764 mg, 0.99 mmol, 99%; $^{31}$P NMR (CDCl$_3$) d 67.87, 67.60; MALDI-TOF MS (positive mode, trihydroxyacetophenone as matrix) [M-H]$^+$ m/z$_{exp}$=713.95, m/z$_{calc}$=714.66; HPLC (7.70 min; Area=88%).

2$^{nd}$ Coupling procedure of 5'-O-DMTr-dG$^{IBu}$-3'-cyanoethyl-phosphoramidite with 5'-OH-T-T-3'-O-Lev cyanoethyl phosphorothioate dimer using the poly(4-vinylpyridinum p-toluenesulfonate) (Aldrich) providing the 5'-O-DMTr-dG$^{IBu}$-3'-cyanoethyl-phosphite-T-3'-cyanoethyl-thionophosphotriester-T-3'-O-Lev trimer:

5'-OH-T-T-3'-O-Lev cyanoethyl phosphorothioate (764 mg, 0.99 mmol) and 5'-O-DMTr-dG$^{IBu}$-3'-cyanoethyl-phosphoramidite (1400 mg, 1.7 mmol, 1.7 eq) are dissolved in anhydrous dichloromethane (20 ml). The solution is transferred under argon in a flask containing the poly(4-vinylpyridinum p-toluenesulfonate) (3.0 g, 10 mmol tos$^-$, 10 eq) and is shaken for 2 h 50 min. Water (50 mL) is added to hydrolyze the remaining phosphoramidite. After 1 h 20 min the resin is filtered off. The reaction is followed by reverse phase HPLC and $^{31}$P NMR. The yield is determined by HPLC. The desired 5'-O-DMTr-dG$^{IBu}$-3'-cyanoethyl-phosphite-T-3'-cyanoethyl-thionophosphotriester-T-3'-O-Lev trimer (HPLC at 11.65 min; Area=72%) is obtained with 100% of yield compared to the 5'-OH-T-T-3'-O-Lev cyanoethyl phosphorothioate (HPLC at 7.70 min; Area=0%). The crude is a mixture of 5'-O-DMTr-dG$^{IBu}$-3'-cyanoethyl-phosphite-T-3'-cyanoethyl-thionophosphotriester-T-3'-O-Lev trimer $^{31}$P NMR (CDCl$_3$) (d 142.78, 142.67, 141.54, 141.50, 68.47, 68.39, 68.16, 67.93) and 5'-O-DMTr-dG$^{IBu}$-3'-cyanoethyl hydrogenophosphonate (d 8.59, 8.05).

2$^{nd}$ Sulfurization: To a solution of 5'-O-DMTr-dG$^{IBu}$-3'-cyanoethyl-phosphite-T-3'-cyanoethyl-thionophosphotriester-T-3'-O-Lev trimer (0.99 mmol) in anhydrous dichloromethane is added AMBERLYST A26 tetrathionate form (2.78 g, 5.0 mmol S$_4$O$_6^{2-}$, 5 eq.). The reaction mixture is shaken for 18 h 45 min. The reaction is followed by reverse phase HPLC and $^{31}$P NMR. The yield is determined by HPLC. After filtration of the resin the desired dG-T-T phosphorothloate triester trimer (HPLC at 11.66 min; Area=58%) is obtained with 100% of yield compared to the 5'-OH-T-T-3'-O-Lev cyanoethyl phosphorothloate. The crude is a mixture of 5'-DMTr-dG$^{IBu}$-T-T-3'-O-Lev cyanoethyl phosphorothioate triester trimer $^{31}$P NMR (CDCl$_3$) (d 68.94, 68.43, 68.09, 67.93, 67.69, 67.34); MALDI-TOF MS (positive mode, trihydroxyacetophenone as matrix) [M-H]$^+$ m/z$_{exp}$=1484.81, m/z$_{calc}$=1485.47 and 5'-O-DMTr-dG$^{IBu}$-3'-cyanoethyl hydrogenophosphonate (d 8.59, 8.52).

2$^{nd}$ Detritylation: To a solution of 5'-DMTr-dG$^{IBu}$-T-T-3'-O-Lev cyanoethyl phosphorothioate triester trimer (0.99 mmol) in 75 ml CH$_2$Cl$_2$/CH$_3$OH (7/3) is added 4 ml (2.5 mmol, 2.5 eq.) of a solution of benzene sulfonic acid 10% in CH$_2$Cl$_2$/CH$_3$OH (7/3). The solution is stirred 40 min at 0° C. The reaction is washed with 10 ml of a saturated solution of NaHCO$_3$, the organic layer is separated, dried (MgSO$_4$) and evaporated. The crude product is dissolved in 8 mL dichloromethane and added to 50 mL diethylether at 0° C. to give a white precipitate. Yield: 1257 mg, 0.78 mmol, 79%; $^{31}$P NMR (CDCl$_3$) d 68.32, 68.07, 68.01, 67.95, 67.86, 67.51, 67.25; MALDI-TOF MS (positive mode, trihydroxyacetophenone as matrix) [M−H]$^+$ m/z$_{exp}$=1182.12, m/z$_{calc}$=1183.09; HPLC (8.94 min; Area=79%).

3$^{rd}$ Coupling procedure of 5'-O-DMTr-dC$^{Bz}$-3'-cyanoethyl-phosphoramidite with 5'OH-dG$^{IBu}$-T-T-3'-O-Lev cyanoethyl phosphorothioate triester trimer using the poly(4-vinylpyridinum p-toluenesulfonate) (Aldrich) providing the 5'-O-DMTr-dC$^{Bz}$-3'-cyanoethyl-phosphite-dG$^{IBu}$-cyanoethyl-thionophosphotriester-T-3'-cyanoethyl-thionophosphotriester-T-3'-O-Lev tetramer:

5'-OH-dG$^{IBu}$-T-T-3'-O-Lev cyanoethyl phosphorothioate triester trimer (1257 mg, 0.78 mmol) and 5'-O-DMTr-dC$^{Bz}$-3'-cyanoethyl-phosphoramidite (1420 mg, 1.7 mmol, 2.2 eq) are dissolved in anhydrous dichloromethane (20 ml). The solution is transferred under argon in a flask containing the poly(4-vinyipyridinum p-toluenesulfonate) (3.0 g, 10 mmol tos$^-$, 12.8 eq) and is shaken for 4 h 50 min. Water (100 mL) is added to hydrolyze the remaining phosphoramidite. After 20 min the resin is filtered off. The reaction is followed by reverse phase HPLC and $^{31}$P NMR. The yield is determined by HPLC. The desired 5'-O-DMTr-dC$^{Bz}$-3'-cyanoethyl-phosphite-dG$^{IBu}$-3'-cyanoethyl-thionophosphotriester-T-3'-cyanoethyl-thionophosphotriester-T-3'-O-Lev tetramer (HPLC at 12.04 min; Area=79%) is obtained with 100% of yield compared to the 5'-OH-dG$^{IBu}$-T-T-3'-O-Lev cyanoethyl phosphorothioate triester trimer (HPLC at 8.94 min; Area=0%). The crude is a mixture of 5'-O-DMTr-dC$^{Bz}$-3'-cyanoethyl-phosphite-dG$^{IBu}$-3'-cyanoethyl-thionophosphotriester-T-3'-cyanoethyl-thionophosphotriester-T-3'-O-Lev tetramer $^{31}$P NMR (CDCl$_3$) (d 141.01, 140.93, 140.05, 139.90, 68.50, 68.09, 68.04, 67.95) and 5'-O-DMTr-dC$^{Bz}$-3'-cyanoethyl hydrogenophosphonate (d 8.15).

3$^{rd}$ Sulfurization: To a solution of 5'-O-DMTr-dC$^{Bz}$-3'-cyanoethyl-phosphite-dG$^{IBu}$-3'-cyanoethyl-thionophosphotriester-T-3'-cyanoethyl-thionophosphotriester-T-3'-O-Lev trimer (0.78 mmol) in anhydrous dichloromethane is added AMBERLYST A26 tetrathionate form (2.78 g, 5.0 mmol S$_4$O$_6^{2-}$, 6.4 eq.). The reaction mixture is shaken for 3 h. The reaction is followed by reverse phase HPLC and $^{31}$P NMR. The yield is determined by HPLC. After filtration of the resin the desired dC-dG-T-T phosphorothioate triester tetramer (HPLC at 121.18 min; Area=73%) is obtained with 100% of yield compared to the 5'-OH-dG$^{IBu}$-T-T-3'-O-Lev cyanoethyl phosphorothioate triester trimer. The crude is a mixture of 5'-DMTr-dC$^{Bz}$-dG$^{IBu}$-T-T-3'-O-Lev cyanoethyl phosphorothioate triester tetramer $^{31}$P NMR (CDCl$_3$) (d 68.51, 68.45, 68.22, 68.18, 68.10, 68.09, 67.70, 67.65); MALDI-TOF MS (positive mode, trihydroxyacetophenone as matrix) [M−H]$^+$ m/z$_{exp}$=1947.90, m/z$_{calc}$=1947.89 and 5'-O-DMTr-dC$^{Bz}$-3'-cyanoethyl hydrogenophosphonate (d 8.09).

3$^{rd}$ Detritytlation: To a solution of 5'-DMTr-dC$^{Bz}$-dG$^{IBu}$-T-T-3'-O-Lev cyanoethyl phosphorothioate triester tetramer (0.78 mmol) in 80 ml CH$_2$O$_2$/CH$_3$OH (7/3) is added 7 ml (4.4 mmol, 5.6 eq.) of a solution of benzene sulfonic acid 10% in CH$_2$Cl$_2$/CH$_3$OH (7/3), The solution is stirred 50 min at 0° C. The reaction is washed with 10 ml of a saturated solution of NaHCO$_3$, the organic layer is separated, dried (MgSO$_4$) and evaporated. The crude product is dissolved in 12 mL CH$_2$Cl$_2$/CH$_3$OH (2/1) and added to 100 mL diethylether at 0° C. to give a white precipitate. Yield: 1334 mg, 0.53 mmol, 68%; $^{31}$P NMR (CDCl$_3$) d 68.50, 68.41, 67.93, 67.86, 67.81, 67.74, 67.71, 67.64, 67.57, 67.51; MALDI-TOF MS (positive mode, trihydroxyacetophenone as matrix) [M−H]$^+$ m/z$_{exp}$=1645.24, m/z$_{calc}$=1645.52; HPLC (9.95 min; Area=68%).

EXAMPLE 33

Synthesis of the dialer 5'-OH-dC$^{Bz}$-dC$^{Bz}$-3'-O-TB-DMS Cyanoethyl Phosphorothioate Triester Coupling procedure of 5'-O-DMTr-dC$^{Bz}$-3'-cyanoethyl-phosphoramidite with 5'-OH-dC$^{Bz}$-3'-O-TBDMS using the poly(4-vinylpyriclinum p-toluenesulfonate) (Aldrich):

5'-OH-dC$^{Bz}$-3'-O-TBDMS (100 mg, 0.22 mmol) and 5'-O-DMTr-dC$^{Bz}$-3'-cyanoethyl-phosphoramidite (384 mg, 0.46 mmol, 2.1 eq) are dissolved in anhydrous acetonitrile (15 ml). The solution is transferred under argon in a flask containing the poly(4-vinylpyridinum p-toluenesulfonate) (690 mg, 2.3 mmol tos$^-$, 10.3 eq) and is shaken for 6 h, The resin is filtered off. The reaction is followed by $^{31}$P NMR. The yield is determined by $^{31}$P NMR. The desired dc-dc phosphite triester dimer is obtained with 100% of yield compared to the 5'-OH-dG$^{IBu}$-3'-O-TBDMS. The crude is a mixture of 5'-O-DMTr-dC$^{Bz}$-dC$^{Bz}$-3'-O-TBDMS cyanoethyl phosphite triester $^{31}$P NMR (CDCl$_3$) (d 141.06, 140.93) and 5'-O-DMTr-dC$^{Bz}$-3'-cyanoethyl hydrogenophosphonate (d 8.67).

Sulfurization: To a solution of 5'-O-DMTr-dC$^{Bz}$-dC$^{Bz}$-3'-O-TBDMS cyanoethyl phosphite triester dimer (0.22 mmol) in anhydrous acetonitrile is added AMBERLYST A26 tetrathionate form (620 mg, 1.2 mmol S$_4$O$_6^{2-}$, 5.4 eq.). The reaction mixture is shaken for 65 h. The reaction is followed by $^{31}$P NMR. The yield is determined by $^{31}$P NMR. After filtration of the resin the desired dC$^{Bz}$-dC$^{Bz}$-phosphorothioate triester dimer is obtained with 100% of yield compared to the 5'-OH-dC$^{Bz}$-3'-O-TBDMS. The crude is a mixture of 5'-O-DMTr-dC$^{Bz}$-dC$^{Bz}$-3'-O-TBDMS cyanoethyl phosphorothioate $^{31}$P NMR (CDCl$_3$) (d 68.24, 68.19) and 5'-O-DMTr-dC$^{Bz}$-3'-cyanoethyl hydrogenophosphortate (d 8.57).

Detritytiation: To a solution of 5'-O-DMTr-dC$^{Bz}$-dC$^{Bz}$-3'-O-TBDMS cyanoethyl phosphorothioate triester (0.22 mmol) in 20 ml CH$_2$Cl$_2$/CH$_3$OH (7/3) is added 0.5 ml (0.3 mmol, 1.3 eq.) of a solution of benzene sulfonic acid 10% in CH$_2$Cl$_2$/CH$_3$OH (7/3). The solution is stirred 30 min at 0° C. Another 0.5 ml (0.3 mmol, 1.3 eq.) of a solution of benzene sulfonic acid 10% in CH$_2$Cl$_2$/CH$_3$OH (7/3) is added and the solution is stirred for 30 min. Another 0.7 ml (0.4 mmol, 1.8 eq.) of a solution of benzene sulfonic acid 10% in CH$_2$Cl$_2$/CH$_3$OH (7/3) is added and the solution is stirred for 30 min. The reaction is washed with 5 ml of a saturated solution of NaHCO$_3$, the organic layer is separated, dried (NaSO$_4$), evaporated and purified on a silica gel column. The desired dimer dC-dC is eluted with CH$_2$Cl$_2$/CH$_3$OH (33/1). Yield: 106 mg, 0.1 mmol, 52%; $^{31}$P NMR (CDCl$_3$) d 67.92, 67.78; MALDI-TOF MS (positive mode, trihydroxyacetophenone as matrix) [M−H]$^+$ m/z$_{exp}$=908.47, m/z$_{calc}$=909.02; HPLC (12.73 min; Area=85%).

EXAMPLE 34

Synthesis of the dimer 5'-OH-dG$^{IBu}$-dA$^{Bz}$-3'-O-Lev Cyanoethyl Phosphorothioate Triester Coupling procedure of 5'-O-DMTr-dG$^{IBu}$-3'-cyanoethyl-phosphoramidite with 5'-OH-dA$^{Bz}$-3'-O-Lev using the poly (4-vinylpyridinum p-toluenesulfonate) (Aldrich):

5'-OH-dA$^{Bz}$-3'-O-Lev (2.235 g, 4.93 mmol) and 5'-O-DMTr-dG$^{IBu}$-3'-cyanoethyl-phosphoramidite (6.13 g, 7.43 mmol, 1.5 eq) are dissolved in anhydrous dichloromethane (100 ml). The solution is transferred under argon in a flask containing the poly(4-vinylpyridinum p-toluenesulfonate) (14.76 g, 49.3 mmol tos⁻, 10 eq) and is shaken for 2 h 45 min. Water (0.2 ml) is added and the mixture is shaken for 1 h 25 min. The resin is filtered off. The reaction is followed by reverse phase HPLC and $^{31}$P NMR. The yield is determined by HPLC. The desired dG-dA phosphite triester dimer (HALC at 11.69 min; Area=65%) is obtained with 100% of yield compared to the 5'-OH-dA$^{Bz}$-3'-O-Lev (HPLC at 7.20 min; Area=0%). The crude is a mixture of 5'-O-DMTr-dG$^{IBu}$-dA$^{Bz}$-3'-O-Lev cyanoethyl phosphite triester $^{31}$P NMR (CDCl₃) (d 140.52, 140.20) and 5'-O-DMTr-dG$^{IBu}$-3'-cyanoethyl hydrogenophosphonate (d 8.59, 8.09).

Sulfurization: To a solution of 5'-O-DMTr-dG$^{IBu}$-dA$^{Bz}$-3'-O-Lev cyanoethyl phosphite triester dimer (4.93 mmol) in anhydrous dichloromethane is added AMBERLYST A26 tetrathionate form (19.7 g, 24.63 mmol $S_4O_5^{2-}$, 5 eq.). The reaction mixture is shaken for 3 h 10 min. The reaction is followed by reverse phase HPLC and $^{31}$P NMR, The yield is determined by $^{31}$P NMR. After filtration of the resin the desired dG-dA phosphorothioate triester dimer is obtained with 100% of yield compared to the 5'-OH-dA$^{BZ}$-3'-O-Lev. The crude is a mixture of 5'-O-DMTr-dG$^{IBu}$-dA$^{Bz}$-3'-O-Lev cyanoethyl phosphorothioate $^{31}$P NMR (CDCl₃) (d 68.45, 67.73) and 5'-O-DMTr-dG$^{IBu}$-3'-cyanoethyl hydrogenophosphonate (d 8.60, 8.04).

Detritylation: To a solution of 5'-O-DMTr-dG$^{IBu}$-dA$^{Bz}$-3'-O-Lev cyanoethyl phosphorothioate triester (4.93 mmol) in 200 ml dichloromethane is added 50 ml methanol and 20 ml (12.6 mmol, 2.6 eq.) of a solution of benzene sulfonic acid 10% in $CH_2Cl_2/CH_3OH$ (7/3). The solution is stirred 40 min at 0° C. Another 6 ml (3.8 mmol, 0.8 eq.) of a solution of benzene sulfonic acid 10% in $CH_2Cl_2/CH_3OH$ (7/3) is added and the solution is stirred for 15 min. Another 4 ml (2.5 mmol, 0.5 eq.) of a solution of benzene sulfonic acid 10% in $CH_2Cl_2/CH_3OH$ (7/3) is added and the solution is stirred for 15 min. The reaction is washed with 70 ml of a saturated solution of NaHCO₃, the organic layer is separated, dried (MgSO₄) and evaporated. The crude product is dissolved in 16 mL dichloromethane and added to 100 ml diethylether at 0° C. to give a white precipitate. Yield: 4.28 mg, 3.8 mmol, 77%; $^{31}$P NMR (CDCl₃) d 68.07, 67.80; MALDI-TOF MS (positive mode, trihydroxyacetophenone as matrix) [M–H]⁺ m/$z_{exp}$=923.08, m/$z_{calc}$=922.89; HPLC (8.90 min and 9.07 min; Area=70%). After complete deprotection with ammonia solution (28% NH₃ in water, 14 h) MALDI-TOF MS (positive mode, trihydroxyacetophenone as matrix) [M–H]⁺ m/$z_{exp}$=597.57, m/$z_{calc}$=596.51; HPLC (8.45 min and 8.77 min; Area=82%).

EXAMPLE 35

Synthesis of the Dimer 5'-DMTr-O-dC$^{Bz}$-dA$^{Bz}$-3'-OH Cyanoethyl Phosphorothioate Triester Coupling procedure of 5'-O-DMTr-dC$^{Bz}$-3'-cyanoethyl-phosphoramidite with 5'-OH-dA$^{Bz}$-3'-O-Lev using the poly (4-vinylpyridinum p-toluenesulfonate) (Aldrich):

5'OH-dA$^{Bz}$-3'-O-Lev (200 mg, 0.44 mmol) and 5'-O-DMTr-dC$^{Bz}$-3'-cyanoethyl-phosphoramidite (626 mg, 0.75 mmol, 1.7 eq) are dissolved in anhydrous dichloromethane (10 ml). The solution is transferred under argon in a flask containing the poly(4-vinylpyridinum p-toluenesulfonate) (1.3 g, 3 mmol tos⁻, 6.8 eq) and is shaken for 8 h. The resin is filtered off. The reaction is followed by reverse phase HPLC and $^{31}$P NMR. The yield is determined by HPLC. The desired dC-dA phosphite triester dimer (HPLC at 13.13 min; Area=63%) is obtained with 100% of yield compared to the 5'-OH-dA$^{Bz}$-3'-O-Lev (HPLC at 7.39 min; Area=0%). The crude is a mixture of 5'-O-DMTr-dG$^{Bz}$-dG$^{Bz}$-3'-O-Lev cyanoethyl phosphite triester $^{31}$P NMR (CDCl₃) (d 140.68, 140.58) and 5'-O-DMTr-dC$^{Bz}$-3'-cyanoethyl hydrogenophosphonate (d 8.04, 8.02), Sulfurization: To a solution of 5'-O-DMTr-dC$^{Bz}$-dA$^{Bz}$-3'-O-Lev cyanoethyl phosphite triester dimer (0.44 mmol) in anhydrous dichloromethane is added AMBERLYST A26 tetrathionate form (2.5 g, 4.38 mmol $S_4O_5^{2-}$, 9.9 eq.). The reaction mixture is shaken for 10 h. The reaction is followed by reverse phase HPLC and $^{31}$P NMR. The yield is determined by $^{31}$P NMR. After filtration of the resin the desired dC-dA phosphorothioate triester dimer is obtained with 100% of yield compared to the 5'-OH-dA$^{Bz}$-3'-O-Lev. The Solvent is removed under reduced pressure. The crude is a mixture of 5'-O-DMTr-dC$^{Bz}$-dA$^{Bz}$-3'-O-Lev cyanoethyl phosphorothioate $^{31}$P NMR (CDCl₃) (d 68.33, 68.30) and 5'-O-DMTr-dC$^{Bz}$-3'-cyanoethyl hydrogenophosphonate (d 8.04, 8.02).

Deprotection of the levulinyl group: The 5'-O-DMTr-dC$^{Bz}$-dA$^{Bz}$-3'-O-Lev cyanoethyl phosphorothioate triester (0.44 mmol) is dissolved in 16 ml pyridine and 4 ml acetic acid. AMBERLYST 15 hydrazine form (1 g, 3.91 mmol $N_2H_5^-$, 8.7 eq.) is added and the solution Is shaken for 1 h 30 min. The reaction is followed by reverse phase HPLC. The yield is determined by reverse phase HPLC. After filtration of the resin the desired dC-dA phosphorothioate triester dimer is obtained with 100% of yield compared to the 5'-OH-dA$^{Bz}$-3'-O-Lev. The Solvent is removed under reduced pressure. The crude is a mixture of 5'-O-DMTr-dC$^{Bz}$-dA$^{Bz}$-3'-OH cyanoethyl phosphorothioate HPLC (12.24 min and 12.45 min; Area=66%) and 5'O-DMTr-dC$^{Bz}$-3'-cyanoethyl hydrogenophosphonate HPLC (10.71 min and 10.82 min; Area=34%). MALDI-TOF MS (positive mode, trihydroxyacetophenone as matrix) [M–H]⁺ m/$z_{exp}$=1120.23, m/$z_{calc}$=1121.16.

SYNTHESIS OF RESINS

EXAMPLE 36

Synthesis of AMBERLYST A26 periodate form 10 g commercial Amberlyst A26 hydroxide form (Rohm & Haas) is washed twice with 20 ml methanol and twice with 20 ml dichloromethane and dried in is vacuum. Potassium tetrathionate (10 g, 47 mmol, 1.4 eq.) is dissolved in 300 ml deionized water. The solution is added to the resin and shaken for 17 hours. The solution is filtered off. Another time Potassium tetrathionate (10 g, 47 mmol, 1.4 eq.) is dissolved in 200 ml deionized water. The solution is added to the resin and shaken for 6 hours. The solution is filtered off. The resin is washed with 1 l deionized water, twice with 30 ml methanol and twice with 30 ml dichloromethane and dried under reduced pressure for 3 hours to give 8.2 g of solid-supported periodate. The reagents loading was determined by elemental analysis, giving a value of 27.16% for iodine (3.40% for nitrogen and 40.20% for carbon, Loading: 2.14 mmol $IO_4^-$ per gram of resin. The resin can be recycled applying the same protocol. Comparable resins are commercially available.

EXAMPLE 37

Synthesis of AMBERLYST 15 hydrazine form 5 g commercial Amberlyst 15 H⁺ form (Aldrich) is washed successively with 20 ml hydrochloric acid and with 500 ml deionized water. Hydrazine (4.38 g, 87.5 mmol, 3.8 eq.) is dissolved in 100 ml deionized water. The solution is added to the resin and shaken for 16 hours. The solution is filtered off. The resin is washed successively with 500 ml deionized water, 50 ml methanol and with 50 ml dichloromethane and dried under reduced pressure for 3 hours to give 5.2 g of solid-supported hydrazine. The reagents loading was determined by elemental analysis, giving a value of 10.94% for nitrogen (12.37% for sulfur and 44.19% for carbon. Loading: 3.91 mmol $N_2H_5^+$ per gram of resin.

EXAMPLE 38

Recycling of poly(4-vinylpyridinum p-toluenesulfonate)

Used poly(4-vinylpyridinum p-toluenesulfonate) (20 g) is washed successively for one hour each with acetonitrile (100 ml), dichloromethane (100 ml) and methanol (100 ml). Then the resin is added to a solution of p-toluene sulfonic acid (40 g, 0.23 mol) in methanol (400 ml) and shaken for 21 h. The solution is filtered off and the resin is washed with methanol (150 ml) and dichloromethane (150 ml) and dried at 80° C. under vacuum over $P_2O_5$ for 8 h. The reagents loading was determined by elemental analysis, giving a value of 10.73% for sulfur and 4.90% for nitrogen. Loading: 3.35 mmol tos⁻ per gram of resin.

SYNTHESIS OF PHOSPHODIESTER OLIGOMERS

Formation of the Phosphate Triester Bridge

In this part, we focus on the formation of natural phosphodiester oligomers. The coupling of the phosphoramidite nucleotide and of the 5'-OH nucleoside was performed with the resin polyvinyl pyridinium p-toluene sulfonate (PVP) commercially available from ALDRICH. The oxidation of the phosphite triester linkage was achieved with the resin polystyrylmethyltrimethylamonium metaperiodate (PS—N$(CH_3)_3^+$ $IO_4^-$) commercially available from NOVABIOCHEM. Then, the detritylation step was performed in solution with BSA. The purification was an extraction in dichloromethane followed by a precipitation in ether.

EXAMPLE 39

Synthesis of the dimer 5'-OH-T-T-3'-O-Lev cyanoethyl phosphate triester

Coupling procedure of 5'-O-DMTr-T-3'-cyanoethyl phosphoramidite with 5'-OH-T-3'-O-Lev using the PVP resin.

A solution of 5'-OH-T-3'-O-Lev (170 mg, 0.5 mmol) and 5'-O-DMTr-T-3'-cyanoethyl phosphoramidite (745 mg, 1 mmol, 2 eq) In anhydrous acetonitrile (15 ml) is added to PVP resin (1.5 g, 5 mmol pyrH⁺, 10 eq). The reaction is followed by reverse phase HPLC. After 5 h the reaction is complete. The desired dimer 5'-O-DMTr-T-T-3'-O-Lev cyanoethyl phosphite triester is characterized by $^{31}$P NMR. The crude is a mixture of 5'-O-DMTr-T-T-3'-O-Lev cyanoethyl phosphite triester (d 140.62, 140.48) and of 5'-O-DMTr-T-3'-cyanoethyl hydrogenophosphonate (d 8.81, 8.76).

Oxidation: The PVP resin is filtered off and the resulting solution is added to PS—N$(CH_3)_3^+$ $IO_4^-$ (1 g, 2.5 mmol $IO_4^-$, 5 eq.). The reaction is followed by $^{31}$P NMR and by reverse phase HPLC. The reaction is complete after 45 min. The desired dimer 5'-O-DMTr-T-T-3'-O-Lev cyanoethyl phosphate triester is characterized by $^{31}$P NMR. The crude is a mixture of 5'-O-DMTr-T-3'-cyanoethyl phosphate diester (d −2.80), 5'-O-DMTr-T-T-3'-O-Lev cyanoethyl phosphate triester (d −1.48, −1.63), 5'-O-DMTr-T-3'-cyanoethyl hydrogenophosphonate (d 8.69, 8.64).

Detritylation: The PS—N$(CH_3)_3^+$ $IO_4^-$ is filtered off and the solvent are evaporated. The crude is dissolved in 8 ml of $CH_2Cl_2/CH_3OH$ (7/3) and cooled in an ice bath. To this solution is added 2 ml of a solution of benzene sulfonic acid 10% in $CH_2Cl_2/CH_3OH$ (7/3). The solution is stirred 45 min at 0° C. The reaction is stopped with 20 ml of a saturated solution of $NaHCO_3$. The aqueous phase is extracted three times with dichloromethane. The organic layer is separated, dried ($Na_2SO_4$) and evaporated under reduce pressure. The residue is dissolved in 5 ml of $CH_2Cl_2$/MeOH (4/1) and added to 50 ml of cooled diethyl ether drop by drop with a strong stirring. The mixture is centrifuged for 45 min and the supernatant is eliminated. The desired 5'-OH-T-T-3'-O-Lev cyanoethyl phosphate triester dimer is obtained with a yield of 75.4% (calculated: 91% per step) compared to the 5'-OH-T-3'-O-Lev. $^{31}$P NMR (CD$_3$CN) d −1.67, −1.72. MALDI-TOF MS (positive mode, trihydroxyacetophenone as matrix) [M+H]⁺ m/z$_{exp}$=700.42, m/z$_{calc}$=698.60. The spectrophotometric purity (91%) is determined by HPLC at 260 nm.

EXAMPLE 40

Synthesis of the Tamer 5'-OH-G$^{IBu}$-T-T-3'-O-Lev Cyanoethyl Phosphate Triester Coupling procedure of 5'-O-DMTr-G$^{IBu}$-3'-cyanoethyl phosphoramidite with 5'-OH-T-T-3'-O-Lev dimer using the PVP resin.

A solution of 5'-OH-T-T-3'-O-Lev (263 mg, 377 mmol) and 5'-O-DMTr-G$^{IBu}$-3'-cyanoethyl phosphoramidite (623 mg, 754 mmol, 2 eq) in anhydrous acetonitrile (15 ml) is added to PVP resin (1.1 g, 3.8 mmol pyrH⁺, 10 eq). The reaction is followed by reverse phase HPLC. After 3 h 30 min the reaction is complete. The desired trimer 5'-O-DMTr-G$^{IBu}$-T-T-3'-O-Lev is characterized by $^{31}$P NMR. The crude is a mixture of 5'-O-DMTr-G$^{IBu}$-T-T-3'-O-Lev trimer (phosphite triester linkage d 141.56, 141.50, 141.44, 141.39, 141.13, 141.05; phosphate triester linkage d −1.35; −1.44, −132, −1.57) and of 5'-O-DMTr-G$^{IBu}$-3'-cyanoethyl hydrogenophosphonate (d 9.03, 8.84).

Oxidation: The PVP resin is filtered off and the resulting solution is added to PS—N$(CH_3)_3^+$ $IO_4^-$ (0.75 g, 1.9 mmol $IO_4^-$, 5 eq.). The reaction is followed by $^{31}$P NMR and by reverse phase HPLC. The reaction is complete after 45 min. The desired dimer 5'-O-DMTr-G$^{IBu}$-T-T-3'-O-Lev cyanoethyl phosphate triester is characterized by $^{31}$P NMR. The crude is a mixture of 5'-O-DMTr-G$^{IBu}$-3'-cyanoethyl phosphate diester (d −2.52), 5'-O-DMTr-G$^{IBu}$-T-T-3'-O-Lev cyanoethyl phosphate triester (d −1.23, −1.35, −1.43, −1.50, −1.55), 5'-O-DMTr-T-3'-cyanoethyl hydrogenophosphonate (d 9.09, 8.90).

Detritylation: The PS—N$(CH_3)_3^+$ $IO_4^-$ is filtered off and the solvent are evaporated. The crude is dissolved in 8 ml of $CH_2Cl_2/CH_3OH$ (7/3) and cooled in an ice bath. To this solution is added 2 ml of a solution of benzene sulfonic acid 10% in $CH_2Cl_2/CH_3OH$ (7/3). The solution is stirred 45 min at 0° C. The reaction is stopped with 20 ml of a saturated solution of $NaHCO_3$. The aqueous phase is extracted three times with dichloromethane. The organic layer is separated, dried ($Na_2SO_4$) and evaporated under reduce pressure. The residue is dissolved in 5 ml of $CH_2Cl_2$/MeOH (4/1) and added to 50 ml of cooled diethyl ether drop by drop with a strong stirring. The mixture is centrifuged for 45 min and the supernatant Is eliminated. The desired 5'-OH-G$^{IBu}$-T-T-3'-O-Lev cyanoethyl phosphate triester trimer is obtained with a yield of 37% (calculated: 72% per step) compared to the 5-OH-T-T-3'-O-Lev. $^{31}$P NMR (CD$_3$CN) d −1.59, −1.68, −1.71, −1.75. MALDI-TOF MS (positive mode, trihydroxyacetophenone as matrix) [M+H]$^+$ m/z$_{exp}$=1149.60, m/z$_{calc}$=1150.96. The spectrophotometric purity (87%) is determined by HPLC at 260 nm.

This low yield is due to the low solubility of the detritylated trimer in dichloromethane, acetonitrile. The trimer is soluble in methanol, and DMF.

EXAMPLE 41

Synthesis of the dimer 5'-OH-T-A$^{Bz}$-3'-O-Lev cyanoethyl phosphate triester

Coupling procedure of 5'-O-DMTr-T-3'-cyanoethyl phosphoramidite with 5'-OH-A$^{Bz}$-3'-O-Lev using the PVP resin.

A solution of 5'-OH-A$^{Bz}$-3'-O-Lev (453 mg, 1 mmol) and 5'-O-DMTr-T-3'-cyanoethyl phosphoramidite (1.49 g, 2 mmol, 2 eq) in anhydrous acetonitrile (20 ml) is added to PVP resin (3 g, 10 mmol pyrH$^+$, 10 eq). The reaction is followed by reverse phase HPLC. After 5 h the reaction is complete. The desired dimer 5'-O-DMTr-T-A$^{Bz}$-3'-O-Lev cyanoethyl phosphite triester is characterized by $^{31}$P NMR. The crude is a mixture of 5'-O-DMTr-T-A$^{Bz}$-3'-O-Lev cyanoethyl phosphite triester (d 140.48, 140.30) and of 5'-O-DMTr-T-3'-cyanoethyl hydrogenophosphonate (d 8.76, 8.71), Oxidation: The PVP resin is filtered off and the resulting solution is added to PS—N(CH$_3$)$_3$$^+$ IO$_4$$^-$ (2 g, 5 mmol IO$_4$$^-$, 5 eq.). The reaction is followed by $^{31}$P NMR and by reverse phase HPLC. The reaction is complete after 15 min, The desired dimer 5'-O-DMTr-T-A$^{Bz}$-3'-O-Lev cyanoethyl phosphate triester is characterized by $^{31}$P NMR. The crude is a mixture of 5'-O-DMTr-T-3'-cyanoethyl phosphate diester ($^{31}$P NMR (CD$_3$CN) d −3.01), 5'-O-DMTr-T-3'-O-Lev cyanoethyl phosphate triester (d −1.58, −1.80), 5'-O-DMTr-T-3'-cyanoethyl hydrogenophosphonate (d 8.76, 8.71).

Detritylation: The PS—N(CH$_3$)$_3$$^+$ IO$_4$$^-$ is filtered off and the solvent are evaporated. The crude is dissolved in 16 ml of CH$_2$Cl$_2$/CH$_3$OH (7/3) and cooled in an ice bath. To this solution is added 4 ml of a solution of benzene sulfonic acid 10% in CH$_2$Cl$_2$/CH$_3$OH (7/3). The solution is stirred 45 min at 0° C. The reaction is stopped with 30 ml of a saturated solution of NaHCO$_3$. The aqueous phase is extracted three times with dichloromethane. The organic layer is separated, dried (Na$_2$SO$_4$) and evaporated under reduce pressure. The residue is dissolved in 10 ml of CH$_2$Cl$_2$/MeOH (4/1) and added to 100 ml of cooled diethyl ether drop by drop with a strong stirring. The mixture is centrifuged for 45 min and the supernatant is eliminated. The desired 5'-OH-T-A$^{Bz}$-3'-O-Lev cyanoethyl phosphate triester dimer is obtained with a yield of 73% (calculated: 90% per step) compared to the 5'-OH-T-3'-O-Lev. $^{31}$P NMR (CD$_3$CN) d −1.77. MALDI-TOF MS (positive mode, trihydroxyacetophenone as matrix) [M+H]$^+$ m/z$_{exp}$=811.72, m/z$_{calc}$=810.45. The spectrophotometric purity (96%) is determined by HPLC at 260 nm,

EXAMPLE 42

Synthesis of the trimer 5'-OH—C$^{Bz}$-T-A$^{Bz}$-3'-O-Lev Cyanoethyl Phosphate Triester Coupling procedure of 5'-O-DMTr-C$^{Bz}$-3'-cyanoethyl phosphoramidite with 5'-OH-T-A$^{Bz}$-3'-O-Lev using the PVP resin.

A solution of 5'OH-T-A$^{Bz}$-3'-O-Lev (618 mg, 0.76 mmol) and 5'-O-DMTr-C$^{Bz}$-3'-cyanoethyl phosphoramidite (1.27 g, 1.52 mmol, 2 eq) in anhydrous acetonitrile (25 ml) and anhydrous DMF (2.5 ml) is added to PVP resin (2.3 g, 7.6 mmol pyrH$^+$, 10 eq). The reaction is followed by reverse phase HPLC. After 2 h 30 the reaction is complete. The desired trimer Lev cyanoethyl phosphite triester is characterized by $^{31}$P NMR. The crude is a mixture of 5'-O-DMTr-C$^{Bz}$-A$^{Bz}$-T-3'-O-Lev trimer (phosphite triester linkage d 140.76, 140.65, 140.09, 140.03; phosphate triester linkage d −1.53, −1.57) and of 5'-O-DMTr-C$^{Bz}$-3'-cyanoethyl hydrogenophosphonate (d 8.73).

Oxidation: The PVP resin is filtered off and the resulting solution is added to PS—N(CH$_3$)$_3$$^+$ IO$_4$$^-$ (1.52 g, 3.8 mmol 104, 5 eq.). The reaction is followed by $^{31}$P NMR and by reverse phase HPLC. The reaction is complete after 15 min. The desired trimer 5'-O-DMTr-C$^{Bz}$-T-A$^{Bz}$-3'-O-Lev cyanoethyl phosphate triester is characterized by $^{31}$P NMR, The crude is a mixture of 5'-O-DMTr-C$^{Bz}$-T-A$^{Bz}$-3'-O-Lev cyanoethyl phosphate triester (d −1.54, −1.59, −162, −1.72), 5'-O-DMTr-C$^{Bz}$-3'-cyanoethyl hydrogenophosphonate (d 8.74).

Detritylation: The PS—N(CH$_3$)$_3$$^+$IO$_4$$^-$ is filtered off and the solvent are evaporated. The crude is dissolved in 32 ml of CH$_2$Cl$_2$/CH$_3$OH (7/3) and cooled in an ice bath. To this solution is added 8 ml of solution of benzene sulfonic acid 10% in CH$_2$Cl$_2$/CH$_3$OH (7/3). The solution is stirred 1 h at 0° C. The reaction is stopped with 40 ml of a saturated solution of NaHCO$_3$. The aqueous phase is extracted three times with dichloromethane. The organic layer is washed with an aqueous solution of Na$_2$S$_2$O$_3$ 0.2 M. The organic layer is separated, dried (Na$_2$SO$_4$) and evaporated under reduce pressure. The residue is dissolved in 10 ml of CH$_2$Cl$_2$ and added to 100 ml of cooled diethyl ether drop by drop with a strong stirring. The mixture is centrifuged for 45 min and the supernatant is eliminated. The desired 5'-OH—C$^{Bz}$-T-A$^{Bz}$-3'-O-Lev cyanoethyl phosphate triester trimer is obtained with a yield of 90% (calculated: 96% per step) compared to the dimer 5'OH-T-A$^{Bz}$-3'-O-Lev. $^{31}$P NMR (CD$_3$CN) d −1.75, −1.79, −1.87, −1.91. MALDI-TOF MS (positive mode, trihydroxyacetophenone as matrix) [M+H]$^+$ m/z$_{exp}$=1257.53, m/z$_{calc}$=1258.08. The spectrophotometric purity (89%) is determined by HPLC at 260 nm.

EXAMPLE 43

Synthesis of the Tetramer 5'-OH-G$^{IBu}$-C$^{Bz}$-T-A$^{Bz}$-3'-O-Lev Cyanoethyl Phosphate Triester Coupling procedure of 5'-O-DMTr-G$^{IBu}$-3'-cyanoethyl phosphoramidite with 5'-OH—C$^{Bz}$-T-A$^{Bz}$-3'-O-Lev using the PVP resin.

A solution of 5'-OH—C$^{Bz}$-T-A$^{Bz}$-3'-O-Lev (866 mg, 0.69 mmol) and 5'-O-DMTr-cyanoethyl phosphoramidite (1.14 g, 1.38 mmol, 2 eq) in anhydrous acetonitrile (25 ml) and anhydrous DMF (2.5 ml) is added to PVP resin (2.1 g, 6.9 mmol pyrH$^+$, 10 eq). The reaction is followed by reverse phase HPLC. After 3 h the reaction is complete, The desired tetramer 5'-O-DMTr-G$^{IBu}$-C$^{Bz}$-A$^{Bz}$-T-3'-O-Lev is characterized by $^{31}$P NMR. The crude is a mixture of 5'-O-DMTr-G$^{IBu}$-C$^{Bz}$-A$^{Bz}$-T-3'-O-Lev tetramer (phosphite triester linkage d 141.86, 141.82, 141.76, 141.61, 140.69, 140.66, 140.61; phosphate triester linkage d −1.53, −1.58, −1.61, −1.64, −1.71, −1.82) and of 5'-O-DMTr-G$^{IBu}$-3'-cyanoethyl hydrogenophosphonate (d 9.01, 8.84).

Oxidation: The PVP resin is filtered off and the resulting solution is added to PS—N(CH$_3$)$_3$$^+$ IO$_4$$^-$ (1.38 g, 3.45 mmol IO$_4$$^-$, 5 eq.). The reaction is followed by $^{31}$P NMR and by reverse phase HPLC. The reaction is complete after 45 min. The desired tetramer 5'-O-DMTr-G$^{IBu}$-C$^{Bz}$-T-A$^{Bz}$-3'-O-Lev cyanoethyl phosphate triester is characterized by $^{31}$P NMR. The crude is a mixture of 5'-O-DMTr-G$^{IBu}$-3'-cyanoethyl phosphate diester ($^{31}$P NMR (CD$_3$CN) d −2.69), 5'-O-DMTr-G$^{IBu}$-C$^{Bz}$-T-A$^{Bz}$-3'-O-Lev cyanoethyl phosphate triester (d −1.38, −1.43, −1.53, −1.60, −1.64), 5'-O-DMTr-C$^{Bz}$-3'-cyanoethyl hydrogenophosphonate (d 9.02, 8.38).

Detritylation: The PS—N(CH$_3$)$_3$$^+$ IO$_4$$^-$ is filtered off and the solvent are evaporated. The crude is dissolved in 32 ml of CH$_2$Cl$_2$/CH$_3$OH (7/3) and cooled in an ice bath. To this solution is added 8 ml of a solution of benzene sulfonic acid 10% in CH$_2$Cl$_2$/CH$_3$OH (7/3). The solution is stirred 1 h 15 at 0° C. The reaction is stopped with 40 ml of a saturated solution of NaHCO$_3$. The aqueous phase is extracted three times with dichloromethane. The organic layer is washed with an aqueous solution of Na$_2$S$_2$O$_3$ 0.2 M. The organic layer is separated, dried (Na$_2$SO$_4$) and evaporated under reduce pressure, The residue is dissolved in 4 ml of CH$_2$Cl$_2$ and added to 100 ml of cooled diethyl ether drop by drop with a strong stirring. The mixture is centrifuged for 45 min and the supernatant is eliminated. The desired 5'-OH-G$^{IBu}$-C$^{Bz}$-T-A$^{Bz}$-3'-O-Lev cyanoethyl phosphate triester tetramer is obtained with a yield of 83% (calculated: 94% per step) compared to the trimer $^{31}$P NMR (CD$_3$CN) d −1.59, −1.69, −1.81. MALDI-TOF MS (positive mode, trihydroxyacetophenone as matrix) [M+H]$^+$ m/$z_{exp}$=1708.44, m/$z_{calc}$=1710.45. The spectrophotometric purity (80%) is determined by HPLC at 260 nm.

EXAMPLE 44

Synthesis of the Pentamer 5'-OH-A$^{Bz}$-G$^{IBu}$-C$^{Bz}$-T-A$^{Bz}$-3'-O-Lev Cyanoethyl Phosphate Triester Coupling procedure of 5'-O-DMTr-A$^{Bz}$-3'-cyanoethyl phosphoramidite with 5'-OH-G$^{IBu}$-C$^{Bz}$-T-A$^{Bz}$-3'-O-Lev using the PVP resin.

A solution of 5'-OH-G$^{IBu}$-C$^{Bz}$-T-A$^{Bz}$-3'-O-Lev (982 mg, 0.57 mmol) and 5'-O-DMTr-A$^{Bz}$-3'-cyanoethyl phosphoramidite (1.15 g, 1.15 mmol, 2 eq) in anhydrous acetonitrile (20 ml) and anhhydrous DMF (2.5 ml) is added to PVP resin (1.7 g, 5.7 mmol pyrH$^+$, 10 eq). The reaction is followed by reverse phase HPLC. After 3 h the reaction is complete, The desired pentamer 5'-O-DMTr-A$^{Bz}$-G$_{IBu}$-C$^{Bz}$-A$^{Bz}$-T-3'-O-Lev is characterized by $^{31}$P NMR. The crude is a mixture of 5'-O-DMTr-A$^{Bz}$-G$^{IBu}$-C$^{Bz}$-A$^{Bz}$-T-3'-O-Lev pentamer (phosphite triester linkage d 141.00, 140.78, 140.68, 140.16, 139.94; phosphate triester linkage d −1.36, −1.42, −1.46, −1.52, −1.57, −1.67, −1.70, −1.82) and of 5'-O-DMTr-A$^{Bz}$-3'-cyanoethyl hydrogenophosphonate (d 8.76, 8.71).

Oxidation: The PVP resin is filtered off and the resulting solution is added to PS—N(CH$_3$)$_3$$^+$ IO$_4$$^-$ (1.2 g, 2.87 mmol IO$_4$$^-$, 5 eq.). The reaction is followed by $^{31}$P NMR and by reverse phase HPLC. The reaction is complete after 45 min. The desired pentamer cyanoethyl phosphate triester is characterized by $^{31}$P NMR. The crude is a mixture of 5'-O-DMTr-A$^{Bz}$-3'-cyanoethyl phosphate diester ($^{31}$P NMR (CD$_3$CN) d −2.67), 5'-O-DMTr-A$^{Bz}$-G$^{IBu}$-C$^{Bz}$-T-A$^{Bz}$-3'-O-Lev cyanoethyl phosphate triester (d −1.24, −1.39, −1.54, −1.66, −1.71), 5'-O-DMTr-A$^{Bz}$-3'-cyanoethyl hydrogenophosphonate (d 8.82). Detritylation: The PS—N(CH$_3$)$_3$$^+$ IO$_4$$^-$ is filtered off and the solvent are evaporated. The crude is dissolved in 50 ml of CH$_2$Cl$_2$, the solution is washed with 50 ml of an aqueous solution of Na$_2$S$_2$O$_3$ 0.2 M. The organic layer is separated, dried (Na$_2$SO$_4$) and evaporated under reduce pressure. The crude is dissolved in 16 ml of CH$_2$Cl$_2$/CH$_3$OH (7/3) and cooled in an ice bath. To this solution is added 4 ml of a solution of benzene sulfonic acid 10% in CH$_2$Cl$_2$/CH$_3$OH (7/3). The solution is stirred 45 min at 0° C. 70 ml of CH$_2$Cl$_2$ and 10 ml of pyridine are added to the solution. The reaction is stopped with 70 ml of a saturated solution of NaHCO$_3$. The aqueous phase is extracted three times with 30 ml of CH$_2$Cl$_2$ and 5 ml of pyridine. The organic layer is separated, dried (Na$_2$SO$_4$) and evaporated under reduce pressure. The residue is dissolved in 5 ml of CH$_2$Cl$_2$/MeOH (4/1) and added to 100 ml of cooled diethyl ether drop by drop with a strong stirring. The mixture is centrifuged for 45 min and the supernatant is eliminated. The desired 5'-OH-A$^{Bz}$-G$^{IBu}$-C$^{Bz}$-T-O-3'-O-Lev cyanoethyl phosphate triester pentamer is obtained with a yield of 85% (calculated: 95% per step) compared to the tetramer 5'OH-G$^{IBu}$-C$^{Bz}$-T-A$^{Bz}$-3'-O-Lev. $^{31}$P NMR (CD$_3$CN) d −1.35, −1.42, −1.55, −1.63. MALDI-TOF MS (positive mode, trihydroxyacetophenone as matrix) [M+H]$^+$ m/$z_{exp}$=2179.40, m/$z_{calc}$=2180.83. The spectrophotometric purity (84%) is determined by HPLC at 260 nm.

Final Deprotection of the Pentamere:

20 mg (9 mmol) of the 5'-OH-A$^{Bz}$-G$^{IBu}$-C$^{Bz}$-T-A$^{Bz}$-3'-O-Lev cyanoethyl phosphate triester pentamer is dissolved in 5 ml of aqueous ammonia solution (30%). After 16 h at 55° C., the ammonia is evaporated. $^{31}$P NMR (D$_2$O) d 0.26, 0.04, −0.03, −0.09. MALDI-TOF MS (negative mode, trihydroxyacetophenone as matrix) [M+]$^-$ m/$z_{exp}$=1486.29, m/$z_{calc}$=1486.03. The spectrophotometric purity (74%) is determined by HPLC at 260 nm.

H-Phosphonate Synthesis

EXAMPLE 45

Synthesis of the dimer 5'-O-DMTr-dG$^{IBu}$-T-3'-O-Lev H-phosphonate

A solution of 5'-OH-T-3'-O-Lev (42.5 mg, 0.125 mmol) and of 5'-O-DMTr-dG$^{IBu}$-H-phosphonate TEA salt (120.7 mg, 0.150 mmol, 1.2 eq) in 2.0 ml of CH$_2$Cl$_2$/py (1:1) is added to polystyrene-bound acid chloride (430.0 mg, 2.1 mmol/g, 6.6 eq) that is suspended in 3.0 ml of the same solvent. The mixture is shaken for 1 h 30 min at room temperature until the disappearance of the monomers. The reaction is monitored by reverse phase HPLC. The resin is filtered, washed with CH$_2$Cl$_2$. The pyridinium salt present in solution is removed by aqueous extraction and the aqueous phase is washed twice with CH$_2$Cl$_2$. The organic fractions are collected, the solvent is evaporated and the pyridine is eliminated by coevaporation with toluene. The isolated product is dried under vacuum. Yield 70%.

$^{31}$P NMR (CD$_2$Cl$_2$) δ 10.20, 8.99 ppm.

MALDI-TOF MS (positive mode, trihydroxyacetophenone as matrix) [M+]$^+$ m/$z_{exp}$=1025.72, m/$z_{calc}$=1027.02.

The spectrophotometrical purity determined by HPLC is 98%.

EXAMPLE 46

Synthesis of the dimer 5'-O-DMTr-dG$^{IBu}$-dC$^{Bz}$-3'-O-Lev H-phosphonate

A solution of 5'-OH-dC$^{Bz}$-3'-O-Lev (53.7 mg, 0.125 mmol) and of 5'-O-DMTr-dG$^{IBu}$-H-phosphonate TEA salt (120.7 mg, 0.150 mmol, 1.2 eq) in 2.0 ml of CH$_2$Cl$_2$/py (1:1) is added to polystyrene-bound acid chloride (430.0 mg, 2.1 mmol/g, 6.6 eq) that is suspended in 3.0 ml of the same solvent. The mixture is shaken for 1 h 30 min at room temperature until the disappearance of the monomers. The reaction is monitored by reverse phase HPLC. The resin is filtered, washed with $CH_2Cl_2$. The pyridinium salt present in solution is removed by aqueous extraction and the aqueous phase is washed twice with $CH_2Cl_2$. The organic fractions are collected, the solvent is evaporated and the pyridine is eliminated by coevaporation with toluene. The isolated product is dried under vacuum. Yield 72%.

$^{31}$P NMR ($CD_2Cl_2$) ä 9.78, 9.16 ppm.

MALDI-TOF MS (positive mode, trihydroxyacetophenone as matrix) $[M+H]^+$ m/$z_{exp}$=1113.16, m/$z_{calc}$=1116.11.

The spectrophotometrical purity determined by HPLC is 99%.

EXAMPLE 47

Synthesis of the dimer 5'-O-DMTr-dC$^{Bz}$-T-3'-O-Lev H-phosphonate

A solution of 5'-OH-T-3'-O-Lev (142.0 mg, 0.417 mmol) and of 5'-O-DMTr-dC$^{Bz}$-H-phosphonate TEA salt (120.0 mg, 0.500 mmol, 1.2 eq) in 4.0 ml of $CH_2Cl_2$/py (1:1) is added to polystyrene-bound acid chloride (830.0 mg, 2.1 mmol/g, 4.2 eq) that is suspended in 4.0 ml of the same solvent. The mixture is shaken for 1 h at room temperature until the disappearance of the monomers. The reaction is monitored by reverse phase HPLC. The resin is filtered, washed with $CH_2Cl_2$. The pyridinium salt present in solution is removed by aqueous extraction and the aqueous phase is washed twice with $CH_2Cl_2$. The organic fractions are collected, the solvent is evaporated and the pyridine is eliminated by coevaporation with toluene. The isolated product is dried under vacuum. Yield 100%.

$^{31}$P NMR ($CD_2Cl_2$) ä 10.16, 8.72 ppm.

MALDI-TOF MS (positive mode, trihydroxyacetophenone as matrix) $[M+H]^+$ m/$z_{exp}$=1020.21, m/$z_{calc}$=1021.01.

The spectrophotometrical purity determined by HPLC is 99%.

EXAMPLE 48

Synthesis of the dimer dG$^{IBu}$-dA$^{Bz}$-3'-O-Lev H-phosphonate

A solution of 5'-OH-dA$^{Bz}$-3'-O-Lev (189.0 mg, 0.417 mmol) and of 5'-O-DMTr-dG$^{IBu}$-H-phosphonate TEA salt (402.0 mg, 0.500 mmol, 1.2 eq) in 4.0 ml of $CH_2Cl_2$/py (1:1) is added to polystyrene-bound acid chloride (830.0 mg, 2.1 mmol/g, 4.2 eq) that is suspended in 4.0 ml of the same solvent. The mixture is shaken for 1 h at room temperature until the disappearance of the monomers. The reaction is monitored by reverse phase HPLC. The resin is filtered, washed with $CH_2Cl_2$. The pyridinium salt present in solution is removed by aqueous extraction and the aqueous phase is washed twice with $CH_2Cl_2$. The organic fractions are collected, the solvent is evaporated and the pyridine is eliminated by coevaporation with toluene. The isolated product is dried under vacuum. Yield 83%.

$^{31}$P NMR ($CD_2Cl_2$) ä 6.80, 670 ppm.

MALDI-TOF MS (positive mode, trihydroxyacetophenone as matrix) $[M+H]^+$ m/$z_{exp}$=1140.30, m/$z_{calc}$=1140.14.

The spectrophotometrical purity determined by HPLC is 85%.

EXAMPLE 49

Synthesis of the dimer 5'-O-DMTr-T-T-3'-O-Lev H-phosphonate

A solution of 5'-OH-T-3'-O-Lev (142.0 mg, 0.417 mmol) and of 5'-O-DMTr-T-H-phosphonate TEA salt (354.8 mg, 0.500 mmol, 1.2 eq) in 4.0 ml of $CH_2Cl_2$/py (1:1) is added to polystyrene-bound acid chloride (830.0 mg, 2.1 mmol/g, 4.2 eq) that is suspended in 4.0 ml of the same solvent, The mixture is shaken for 1 h at room temperature until the disappearance of the monomers. The reaction is monitored by reverse phase HPLC. The resin is filtered, washed with $CH_2Cl_2$. The pyridinium salt present in solution is removed by aqueous extraction and the aqueous phase is washed twice with $CH_2Cl_2$. The organic fractions are collected, the solvent is evaporated and the pyridine is eliminated by coevaporation with toluene. The isolated product is dried under vacuum. Yield 98%.

$^{31}$P NMR ($CD_2Cl_2$) a 9.99, 8.55 ppm.

MALDI-TOF MS (positive mode, trihydroxyacetophenone as matrix) no result

The spectrophotometrical purity determined by HPLC is 99%,

EXAMPLE 50

Synthesis of the trimer 5'-O-DMTr-dG$^{IBu}$-T-T-3'-O-Lev H-phosphonate

Detritylation of 5'-O-DMTr-T-T-3'-O-Lev H-phosphonate

The H-phosphonate dimer 5'-O-DMTr-T-T-3'-O-Lev (115 mg, 0.123 mmol) is dissolved in 4.0 ml of $CH_2O_2$/MeOH (7:3) and cooled in an ice bath. To this solution 1.0 ml of a solution of 10% BSA (benzene sulfonic acid) in $CH_2Cl_2$/MeOH (7:3) is added drop wise under stirring and the progress of the reaction is monitored by TLC. After 15 min the solution is diluted with 20 ml of $CH_2O_2$ and then 0.4 g of poly(4-vinyl-pyridine) are added. The mixture is shaken 5 minutes and the resin is filtered off and washed with $CH_2Cl_2$. The product is purified by precipitation from $CH_2Cl_2$ with ether and dried under vacuum. Yield 94%.

MALDI-TOF MS (positive mode, trihydroxyacetophenone as matrix) no result

The spectrophotometrical purity determined by HPLC is 99%.

Coupling

A solution of 5'-OH-T-T-3'-O-Lev (712 mg, 0.116 mmol) and of 5'-0-DMTr-dG$^{IBu}$-H-phosphonate TEA salt (140.5 mg, 0.174 mmol, 1.5 eq) in 2.0 ml of $CH_2Cl_2$/py (1:1) is added to polystyrene-bound acid chloride (660.0 mg, 2.1 mmol/g, 12 eq) that is suspended in 4.0 ml of the same solvent. The mixture is shaken for 4 h at room temperature until the disappearance of the monomers. The reaction is monitored by reverse phase HPLC. The resin is filtered, washed with $CH_2Cl_2$. The pyridinium salt present in solution is removed by aqueous extraction and the aqueous phase is washed twice with $CH_2Cl_2$. The organic fractions are collected, dried over $Na_2SO_4$, the solvent is evaporated and the pyridine is eliminated by coevaporation with toluene. The isolated product is dried under vacuum. Yield 55%.

$^{31}$P NMR ($CD_2Cl_2$) ä 10.22, 10.07, 9.73, 9.00, 8.84, 8.75, 8.59 ppm.

MALDI-TOF MS (positive mode, trihydroxyacetophenone as matrix) $[M+H]^+$ m/$z_{exp}$=1312.50, m/$z_{calc}$=1315.21.

EXAMPLE 51

Synthesis of the tetramer 5'-O-DMTr-dC$^{Bz}$-dG$^{IBu}$-T-T-3'-O-Lev H-phosphonate Detritylation of 5'-O-DMTr-dG$^{IBu}$-T-T-3'-O-Lev H-phosphonate The H-phosphonate trimer 5'-O-DMTr-dG$^{IBu}$-T-T-3'-O-Lev (84 mg, 0.064 mmol) is dissolved in 4.0 ml of CH$_2$Cl$_2$/MeOH (7:3) and cooled in an ice bath. To this solution 1.0 ml of a solution of 10% BSA (benzene sulfonic acid) in CH$_2$Cl$_2$/MeOH (7:3) is added drop wise under stirring and the progress of the reaction is monitored by TLC. After 15 min the solution is diluted with 20 ml of CH$_2$Cl$_2$ and then 0.4 g of poly(4-vinyl-pyridine) are added. The mixture is shaken 5 minutes and the resin is filtered off and washed with CH$_2$Cl$_2$. The product is purified by precipitation from CH$_2$Cl$_2$ with ether and dried under vacuum. Yield 71%.

MALDI-TOF MS (positive mode, trihydroxyacetophenone as matrix) [M+H]$^+$ m/z$_{exp}$=1012.07, m/z$_{calc}$=1012.84.

The spectrophotometrical purity determined by HPLC is 83%,

Coupling

A solution of 5'-OH-dG$^{IBu}$-T-T-3'-O-Lev H-phosphonate (45.9 mg, 0.045 mmol) and of 5'-O-DMTr-dC-H-phosphonate TEA salt (54.3 mg, 0.068 mmol, 1.5 eq) in 1.0 ml of CH$_2$Cl$_2$/py (1:1) is added to polystyrene-bound acid chloride (260.0 mg, 2.1 mmol/g, 12 eq) that is suspended in 1.5 ml of the same solvent. The mixture is shaken for 3 h and 30 minutes at room temperature until the disappearance of the monomers. The reaction is monitored by reverse phase HPLC. The resin is filtered, washed with CH$_2$Cl$_2$. The pyridinium salt present in solution is removed by aqueous extraction and the aqueous phase is washed twice with CH$_2$Cl$_2$. The organic fractions are collected, dried over Na$_2$SO$_4$, the solvent is evaporated and the pyridine is eliminated by coevaporation with toluene. The isolated product is dried under vacuum. Yield 75%.

$^{31}$P NMR (CD$_2$Cl$_2$) ä 11.58, 11.11, 10.52, 10.32, 10.14, 9.66, 9.40, 9.14, 8.99, 8.35, 7.40, 7.17, 6.99 ppm.

MALDI-TOF MS (positive mode, trihydroxyacetophenone as matrix) [M+H]$^+$ m/z$_{exp}$=1690.10, m/z$_{calc}$=1692.51.

The spectrophotometrical purity determined by HPLC is 92%.

EXAMPLE 52

Synthesis of the dimer 5'-O-DMTr-dC$^{Bz}$-dA$^{Bz}$-3'-O-Lev H-phosphonate

A solution of 5'-OH-dA$^{Bz}$-3'-O-Lev (197.3 mg, 0.435 mmol) and of 5'-O-DMTr-dC$^{Bz}$-H-phosphonate TEA salt (400.0 mg, 0.500 mmol) in 4.0 ml of CH$_2$Cl$_2$/py (1:1) is added to polystyrene-bound acid chloride (830.0 mg, 2.1 mmol/g, 4.2 eq) that is suspended in 4.0 ml of the same solvent. The mixture is shaken for 1 h at room temperature until the disappearance of the monomers. The reaction is monitored by reverse phase HPLC. The resin is filtered, washed with CH$_2$Cl$_2$. The pyridinium salt present in solution is removed by aqueous extraction and the aqueous phase is washed twice with CH$_2$Cl$_2$. The organic fractions are collected, the solvent is evaporated and the pyridine is eliminated by coevaporation with toluene. The isolated product is dried under vacuum. Yield 95%.

$^{31}$P NMR (CD$_2$Cl$_2$) ä 9.94, 8.94 ppm.

MALDI-TOF MS (positive mode, trihydroxyacetophenone as matrix) [M+H]$^+$ m/z$_{exp}$=1132.14, m/z$_{calc}$=1134.13.

The spectrophotometrical purity determined by HPLC is 96%.

EXAMPLE 53

Synthesis of the trimer 5'-O-DMTr-dG$^{IBu}$-dC$^{Bz}$-dA$^{Bz}$-3'-O-Lev H-phosphonate Detritylation of 5'-O-DMTr-dC$^{Bz}$-dA$^{Bz}$-3'-O-Lev H-phosphonate The H-phosphonate dimer 5'-O-DMTr-dC$^{Bz}$-dA$^{Bz}$-3'-O-Lev (180 mg, 0.158 mmol) is dissolved in 4.0 ml of CH$_2$Cl$_2$/MeOH (7:3) and cooled in an ice bath. To this solution 1.0 ml of a solution of 10% BSA (benzene sulfonic acid) in CH$_2$Cl$_2$/MeOH (7:3) is added drop wise under stirring and the progress of the reaction is monitored by TLC. After 15 min the solution is diluted with 20 ml of CH$_2$Cl$_2$ and then 0.4 g of poly(4-vinyl-pyridine) are added. The mixture is shaken 5 minutes and the resin is filtered off and washed with CH$_2$Cl$_2$. The product is purified by precipitation from CH$_2$Cl$_2$ with ether and dried under vacuum. Yield 83%.

MALDI-TOF MS (positive mode, trihydroxyacetophenone as matrix) [M+H]$^+$ m/z$_{exp}$=831.91, m/z$_{calc}$=831.75.

The spectrophotometrical purity determined by HPLC is 74%.

Coupling

A solution of 5'-OH-dC$^{Bz}$-dA$^{Bz}$-3'-O-Lev (109 mg, 0.131 mmol) and of 5'-O-DMTr-dG$^{IBu}$-H-phosphonate TEA salt (126.5 mg, 0.157 mmol, 1.2 eq) in 2.0 ml of CH$_2$Cl$_2$/py (1:1) is added to polystyrene-bound acid chloride (660.0 mg, 2.1 mmol/g, 6 eq) that is suspended in 3.5 ml of the same solvent. The mixture is shaken for 4 h at room temperature until the disappearance of the monomers. The reaction is monitored by reverse phase HPLC. The resin is filtered, washed with CH$_2$Cl$_2$. The pyridinium salt present in solution is removed by aqueous extraction and the aqueous phase is washed twice with CH$_2$Cl$_2$. The organic fractions are collected, dried over Na$_2$SO$_4$, the solvent Is evaporated and the pyridine is eliminated by coevaporation with toluene. The isolated product Is dried under vacuum. Yield 50%.

$^{31}$P NMR (CD$_2$Cl$_2$) ä 10.24, 10.06, 9.96, 9.88, 9.44, 9.38, 9.33, 9.28 ppm.

MALDI-TOF MS (positive mode, trihydroxyacetophenone as matrix) [M+H]$^+$ m/z$_{exp}$=1516.14, m/z$_{calc}$=1517.43.

The spectrophotometrical purity determined by HPLC is 74%.

EXAMPLE 54

Synthesis of dimer 5'-O-DMTr-T-dG$^{IBu}$-3'-O-lev-H-phosphonate

A solution of 5'-OH-dG$^{IBu}$-3'-O-Lev (435 mg, 1.0 mmol) and of 5'-O-DMTr-dT-H-phosphonate TEA salt (850 mg, 1.2 mmol) in 7.0 ml of CH$_2$Cl$_2$/py (1:1, v/v) is added to polystyrene-bound acid chloride (1.5 g, 2.4 mmol/g, 3 eq) that is suspended in 7.0 ml of the same solvent. The mixture is shaken for 2 h 15 at room temperature until the disappearance of the monomers. The reaction is monitored by reverse phase HPLC. The resin is filtered, washed with CH$_2$Cl$_2$. The pyridinium salt present in solution is removed by aqueous extraction and the aqueous phase is washed twice with $CH_2Cl_2$. The organic fractions are collected, the solvent is evaporated and the pyridine is eliminated by coevaporation with toluene. The isolated product is dried under vacuum. 914 mg Yield 89%.

$^{31}$P NMR ($CD_2Cl_2$) ä 12.63, 8.92 ppm.

MALDI-TOF MS (positive mode, trihydroxyacetophenone as matrix) $[M+H]^+$ $m/z_{exp}$=1026.6, $m/z_{calc}$=1027.0. The spectrophotometrical purity determined by HPLC is 96%.

EXAMPLE 55

Synthesis of the trimer 5'-O-DMTr-$C^{bz}$-T-$dG^{Ibu}$-3'-O-lev H-phosphonate

Detritylation of 5'-O-DMTr-T-$dG^{Ibu}$-3'-O-lev H-phosphonate

The H-phosphonate dimer 5'-O-DMTr-T-$dG^{Ibu}$-3'-O-Lev (430 mg, 0.420 mmol) is dissolved in M ml of $CH_2Cl_2$/MeOH (7:3, v/v) and cooled in an ice bath. To this solution 2.0 ml of a solution of 10% BSA (benzene sulfonic acid) in $CH_2Cl_2$/MeOH (7:3, v/v) is added drop wise under stirring and the progress of the reaction is monitored by TLC. After 20 min the solution is diluted with 50 ml of $CH_2Cl_2$ and then 0.8 g of poly(4-vinyl-pyridine) are added. The mixture is shaken 5 minutes and the resin is filtered off and washed with $CH_2Cl_2$. The product is purified by precipitation from $CH_2Cl_2$ with ether and dried under vacuum. 320 mg Yield 100%. The spectrophotometrical purity determined by HPLC is 98%.

Coupling

A solution of 5'-OH-T-dGibu-3'-O-Lev (320 mg, 0.43 mmol) and of 5'-O-DMTr-$dG^{IBu}$-H-phosphonate TEA salt (413 mg, 0.52 mmol, 1.2 eq) in 4.5 ml of $CH_2Cl_2$/py (1:1, v/v) is added to polystyrene-bound acid chloride (1050 mg, 2.4 mmol/g, 5 eq) that is suspended in 4.5 ml of the same solvent. The mixture is shaken for 4 h at room temperature until the disappearance of the monomers. The reaction is monitored by reverse phase HPLC, The resin is filtered, washed with $CH_2Cl_2$. The pyridinium salt present in solution is removed by aqueous extraction and the aqueous phase is washed twice with $CH_2Cl_2$. The organic fractions are collected, dried over $Na_2SO_4$, the solvent is evaporated and the pyridine is eliminated by coevaporation with toluene. The product is purified by precipitation from $CH_2Cl_2$ with ether and dried under vacuum. 538 mg Yield 89%.

$^{31}$P NMR ($CD_2Cl_2$) ä 12.68, 12.46, 10.27, 9.46, 9.40, 9.11, 8.96, 8.92. ppm.

MALDI-TOF MS (positive mode, trihydroxyacetophenone as matrix) $[M+H]^+$ $m/z_{exp}$=1404.0, $m/z_{calc}$=1404.3. The spectrophotometrical purity determined by HPLC is 94%.

EXAMPLE 56

Synthesis of the trimer 5'-O-DMTr-$C^{bz}$-T-$dG^{Ibu}$-3'-O-lev S-phenyl phosphotriester To a solution of 5'-O-DMTr-$C^{bz}$-T-$dG^{Ibu}$-3'-O-lev H-phosphonate (110 mg, 0.078 mmol) in 2 ml of $CH_2Cl_2$/py (1:1), N-(phenylsulfanyl)phthalimide (80 mg, 0.314 mmol, 4 eq) and Triethylamine (200 mL, 10 eq) were added. The reaction is stirred for 3 h at room temperature. The solvent is evaporated. The product is purified by precipitation from $CH_2Cl_2$ with ether and dried under vacuum. 117 mg Yield 92%

$^{31}$P NMR signals between 24.09 and 25.76 ppm

MALDI-TOF MS (positive mode, trihydroxyacetophenone as matrix) $[M+H]^+$ $m/z_{exp}$=1621.8, $m/z_{calc}$=1620.6. The spectrophotometrical purity determined by HPLC is 87%.

EXAMPLE 57

Synthesis of the trimer 5'-O-DMTr-$C^{bz}$-T-$dG^{Ibu}$-3'-O-lev S-cyanoethyl phosphotriester The trimer 5'-O-DMTr-$C^{bz}$-T-$dG^{Ibu}$-3'-O-lev H-phosphonate (118 mg, 0.084 mmol) is coevaporated twice with dry pyridine (2×2 ml) and dissolved in 2 ml of $CH_2Cl_2$/py (1:1). To this solution is added successively triethylamine (6 mL, 0.5 eq), trimethylsilyl chloride (100 mL, 0.84 mmol, 10 eq) and N-[(2-cyanoethyl)thio]phthalimide (78 mg, 0.336 mmol, 10 eq). After 1 h 30 the reaction is complete. The pyridinium salt present in solution is removed by aqueous extraction and the aqueous phase is washed twice with $CH_2Cl_2$. The solvent is evaporated. The product is purified by precipitation from $CH_2Cl_2$ with ether and dried under vacuum. 106 mg Yield 80%

$^{31}$P NMR signals between 26.86 and 28.75 ppm.

MALDI-TOF MS (positive mode, trihydroxyacetophenone as matrix) $[M+H]^+$ $m/z_{exp}$=1574.6, $m/z_{calc}$=1574.6. The spectrophotometrical purity determined by HPLC is 84%.

EXAMPLE 58

General Procedure for the Synthesis of 5'-OH-3'-O-Lev Cyanoethyl Phosphorothionotriester Base Protected Dimers Using the Phosphoramidite Method on 10 Mmol Scale Coupling procedure of 5'-O-DMTr-3'-cyanoethyl-phosphoramidite base protected nucleotide with 5'-OH-3'-O-Lev base protected nucleoside using the poly(4-vinylpyridinum p-toluenesulfonate) (Aldrich): 5'-OH-3'-O-Lev base protected nucleoside (10 mmol) and 5'-O-DMTr-3'-cyanoethyl-phosphoramidite base protected nucleotide (15 mmol, 1.5 eq) are dissolved in anhydrous dichloromethane (100 ml). The solution is transferred under argon in a flask containing the poly(4-vinylpyridinum p-toluenesulfonate) (100 mmol PyrH$^{30}$, 10 eq.) and shaken. The reaction is followed by reverse phase HPLC and is usually complete between 1 h 30 and 2 h 30. The desired 5'-O-DMTr-3'-O-Lev cyanoethyl phosphite triester base protected dimer is characterized by $^{31}$P NMR. The crude is a mixture of 5'-O-DMTr-3'-O-Lev cyanoethyl phosphite triester base protected dimer and of 5'-O-DMTr-3'-cyanoethyl H-phosphonate base protected nucleotide. The poly(4-vinylpyridinum p-toluenesulfonate) is filtered off, washed 3 times with 50 ml of $CH_2Cl_2$ and the solution is concentrated to 100 ml.

Sulfurization: To the resulting solution is added AMBERLYST A26 tetrathionate form (50 mmol $S_4O_6^{2-}$, 5 eq.), and the reaction mixture is shaken. The reaction is followed by reverse phase HPLC and $^{31}$P NMR and is usually complete between 1 h 30 and 2 h 30. The crude is a mixture of 5'-O-DMTr-3'-O-Lev cyanoethyl phosphorothionotriester base protected dimer and 5'-O-DMTr-3'-cyanoethyl diester H-phosphonate base protected nucleotide. The resin AMBERLYST A26 tetrathionate form is filtered off and washed 3 times with 50 ml of $CH_2Cl_2$.

| dimers 5'-O-DMTr-Nu- | phosphite triester | | phosphorothionotriester | |
|---|---|---|---|---|
| Nu-3'-O-Lev | RT (min) | $^{31}$P NMR d | RT (min) | $^{31}$P NMR d |
| $A^{Bz}$-$A^{Bz}$ | 17.81 | 140.64; 140.46 | 18.23 | 68.30; 68.24 |

-continued

| dimers 5'-O-DMTr-Nu- | phosphite triester | | phosphorothionotriester | |
|---|---|---|---|---|
| Nu-3'-O-Lev | RT (min) | $^{31}$P NMR d | RT (min) | $^{31}$P NMR d |
| $C^{Bz}$-$A^{Bz}$ | 19.09 | 140.48; 140.39 | 19.35, 19.61* | 68.31; 68.26 |
| $G^{IBu}$-T | 15.95; 16.14* | 143.50; 141.71 | 16.73; 17.01* | 68.65; 68.19 |
| $G^{IBu}$-$A^{Bz}$ | 16.86 | 140.34; 140.02 | 17.30; 17.56* | 67.57; 67.41 |

*mixture of Sp and Rp diastereoisomeres

Detritytiation: To the previous solution is added 100 ml of MeOH so that the CH$_2$Cl$_2$/MeOH ratio is about 7/3. The mixture is cooled at 0° C. To the resulting solution is added 90 ml (56 mmol, 5.6 eq.) of a solution of benzene sulfonic acid 10% in CH$_2$Cl$_2$/CH$_3$OH (7/3). The solution is stirred at 0° C. The detrityladon is monitored by TLC and reverse phase HPLC. The reaction time is between 30 min and 1 h, When the reaction is complete, 100 ml of H$_2$O is added to the mixture, the solution is shaken for 10 min at 0° C. Then, the reaction is stopped by stirring at 0° C. for 10 min with 100 ml of a saturated solution of NaHCO$_3$. The solution is diluted with 300 ml of CH$_2$Cl$_2$. The organic layer is then washed up to 4 times with H$_2$O/saturated solution of NaHCO$_3$ in water (1/1), dried with Na$_2$SO$_4$, (50 g) and evaporated. The crude product is dissolved in 50 ml CH$_2$Cl$_2$ and added dropwise to 1 l of diethylether at 0° C. to give a is white precipitate of the pure desired 5'-OH-3'-O-lev cyanoethyl phosphorothionotriester base protected dimer. The solid is filtered off, washed with 500 ml diethylether and dried under vacuum. The dimer is characterized by $^{31}$P NMR and by MALDI-TOF. The spectrophotometric purity is determined by reverse phase HPLC at 260 nm.

| Dimers 5'-OH-Nu-Nu-3'-O-Lev | MW (g/mol) | $^{31}$P-NMR | RT (min) | Yield | HPLC-Purity |
|---|---|---|---|---|---|
| $A^{Bz}$-$A^{Bz}$ | 939.91 | 68.11; 68.06* | 10.85 | 91% (9.5 g) | 91% |
| $C^{Bz}$-$A^{Bz}$ | 915.88 | 68.03; 67.80* | 11.32; 11.46* | 94% (8.7 g) | 91% |
| $G^{IBu}$-T | 808.77 | 68.48; 68.09* | 9.72 | 91% (7.4 g) | 91% |
| $G^{IBu}$-$A^{Bz}$ | 921.89 | 68.02; 67.80* | 10.32; 10.68* | 98% (10.3 g) | 92% |

*mixture of Sp and Rp diastereoisomeres

HPLC-Gradient [column: Macherey-Nagel Nucleosil 100-5 C18]:

0 to 5 min→10% of CH$_3$CN to 40% of CH$_3$CN (in TEAAc 50 mM)

5 to 20 min→40% of CH$_3$CN to 80% of CH$_3$CN (in TEAAc 50 mM)

20 to 25 min→80% of CH$_3$CN to 100% of CH$_3$CN (in TEAAc 50 mM)

The invention claimed is:
1. A method comprising the steps of, in a first cycle,
a) providing a first compound having the formula:

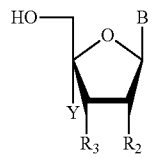

wherein
B is a nucleobase,
Y is H or forms a C4'-O2' methylene linkage with R$_2$,
R$_2$ is H, a protected 2'-hydroxyl group, F, a protected amino group, an O-alkyl group, an O-substituted alkyl, a substituted alkylamino, or forms a C4'-O2' methylene linkage with Y,
R$_3$ is OR'$_3$, NHR"$_3$, NR"$_3$R'"$_3$, a 3'-protected 5'-nucleotidyl group, or a 3'-protected 5'-oligonucleotidyl group,
R'$_3$ is a hydroxyl protecting group, and
R"$_3$, R'"$_3$ are independently an amine protecting group;
b) providing a second compound having the formula:

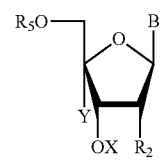

wherein
X comprises a P(III) phosphorus atom,
Y is H or forms a C4'-O2' methylene linkage with R$_2$,
B is a nucleobase,
R$_2$ is H, a protected 2'-hydroxyl group, F, a protected amino group, an O-alkyl group, an O-substituted alkyl, a substituted alkylamino or a C4'-O2' methylene linkage, and
R$_5$ is a hydroxyl protecting group, a 5'-protected 3'-nucleotidyl group, or a 5'-protected 3'-oligonucleotidyl group;
c) reacting the first compound with the second compound in the presence of a solid supported activator to produce 3'-5'-protected elongated oligonucleotide comprising an internucleotide linkage comprising a P(III) phosphorus atom;
d) optionally modifying the 3'-5'-protected elongated oligonucleotide by either or both of steps d1) and d2) in any sequence:
  d1) reacting the 3'-5'-protected elongated oligonucleotide with a solid supported capping reagent;
  d2) reacting the 3'-5'-protected elongated oligonucleotide with a solid supported oxidizing reagent to provide an internucleotide linkage comprising a P(V) phosphorus atom;
e) removing the 5'-protection group by reacting the 3'-5'-protected elongated oligonucleotide with (i) a solid supported deprotection reagent or (ii) a deprotection reagent followed by addition of a solid supported scavenger, to produce a 3'-protected elongated oligonucleotide; and
f) in a second cycle, repeating steps a) to e) wherein the first compound provided in step a) of the second cycle is the 3'-protected elongated oligonucleotide of step e) of the first cycle.

2. The method of claim 1, wherein the second compound of step b) is a phosphoramidite or a H-phosphonate.

3. The method of claim 1 wherein the solid supported activator of step c) is selected from the group consisting of a solid support bearing a pyridinium salt, a cation exchange solid support with an optionally substituted pyridinium salt, a cation exchange solid support with an optionally substituted imidazolium salt, a solid support bearing an optionally substituted azole selected from the group consisting of imidazole, triazole, and tetrazole, a salt of a weak base anion exchange resin with a strong acid, a weak cation exchange resin (carboxylic) in its protonated form, a solid support bearing an optionally substituted phenol, and wherein the solid supported capping reagent of step d1) is selected from the group consisting of a solid supported carboxylic acid chloride, a solid supported carboxylic acid bromide, a solid supported sulfonic acid chloride, a solid supported sulfonic acid, a solid supported chloroformate, a solid supported bromoformate, a solid supported chlorosulfite, a solid supported bromosulfite, a solid supportedphosphorochloridate, a solid supported phosphorobromidate, and a solid supported carbodiimide.

4. The method of claim 1, wherein the solid supported oxidizing reagent is selected from the group consisting of solid supported periodate, solid supported permanganate, solid supported osmium tetroxide, solid supported dichromate, solid supported hydroperoxide, solid supported substituted alkylamine oxide, solid supported percarboxylic acid, and solid supported persulfonic acid.

5. The method of claim 1, wherein the solid supported oxidizing reagent is a solid supported sulfurization reagent.

6. The method of claim 5, wherein the solid supported sulfurization reagent is selected from the group consisting of a solid supported tetrathionate, a solid supported alkyl or aryl sulfonyl disulfide, a solid supported optionally substituted dibenzoyl tetrasulfide, a solid supported bis(alkyloxythiocarbonyl)tetrasulfide, a solid supported optionally substituted phenylacetyl disulfide, a solid supported N-[(alkyl or aryl) sulfanyl]alkyl or aryl substituted succinimide, and a solid supported (2-pyridinyldithio)alkyl or aryl.

7. The method of claim 1, wherein the solid supported capping reagent is a solid supported activated acid, a solid supported carboxylic acid chloride, a solid supported carboxylic acid bromide, a solid supported azolide, a solid supported substituted azolide, a solid supported anhydride, a solid supported chloroformate, a solid supported phosphorochloridate, a solid supported phosphoramidite, or a solid supported H-phosphonate monoester.

8. The method of claim 1, wherein $R_5$ is a dimethoxytrityl group (DMTr) or a monomethoxytrityl group (MMTr) and the solid supported deprotection reagent of step e) is a cationic ion exchanger resin in the H$^+$ form or solid supported ceric ammonium nitrate.

9. The method of claim 1, wherein R'$_3$ is a silyl group and the solid supported deprotection reagent of step e) is a solid supported ammonium fluoride.

10. The method of claim 1, wherein R'$_3$ is a silyl group and the solid supported deprotection reagent of step e) is a solid supported hydrazine or a solid supported hydrazinium.

11. A method comprising the steps of, in a first cycle,
a) providing a first compound having the formula:

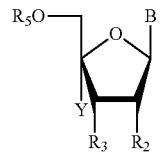

wherein
B is a nucleobase,
Y is H or forms a C4'-O2' methylene linkage with $R_2$,
$R_2$ is H, a protected 2'-hydroxyl group, F, a protected amino group, an O-alkyl group, an O-substituted alkyl, a substituted alkylamino, or forms a C4'-O2' methylene linkage with Y,
$R_3$ is OH or $NH_2$,
$R_5$ is a hydroxyl protecting group, a 5'-protected 3'-nucleotidyl group, or a 5'-protected 3'-nucleotidyl;
b) providing a second compound having the formula:

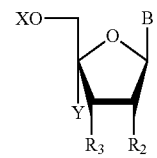

wherein
X comprises a P(III) phosphorus atom,
Y is H or forms a C4'-O2' methylene linkage with R2,
B is a nucleobase,
$R_2$ is H, a protected 2'-hydroxyl group, F, a protected amino group, an O-alkyl group, an O-substituted alkyl, a substituted alkylamino, or forms a C4'-O2' methylene linkage with Y,
$R_3$ is OR'$_3$, NHR"$_3$, NR"$_3$R'"$_3$,
R'$_3$ is a hydroxyl protecting group, a 3'-protected 5'-nucleotidyl group, or a 3'-protected 5'-oligonucleotidyl group, and
R"$_3$ and R'"$_3$ are independently an amine protecting group;
c) reacting the first compound with the second compound in the presence of a solid supported activator to produce a 5'-3'-protected elongated oligonucleotide comprising an internucleotide linkage comprising a P(III) phosphorus atom;
d) optionally modifying the 5'-3'-protected elongated oligonucleotide by either or both of steps d1) and d2) in any sequence;
d1) reacting the 5'-3'-protected elongated oligonucleotide with a solid supported capping reagent;
d2) reacting the 5'-3'-protected elongated oligonucleotide with a solid supported oxidizing reagent to provide an internucleotide linkage comprising a P(V) phosphorus atom;
e) removing the 3'-protection group by reacting the 5'-3'-protected elongated oligonucleotide with (i) a solid supported deprotection reagent or (ii) a deprotection reagent followed by addition of a solid supported scavenger, to produce a 5'-protected elongated oligonucleotide; and
f) in a second cycle, repeating steps a) to e) at least once wherein the 5'-protected compound provided in step a) of the second cycle is the 5'-protected elongated oligonucleotide of step d).

12. The method of claim 11, wherein the second compound of step b) is a phosphoramidite or a H-phosphonate.

13. The method of claim 11 wherein the solid supported activator of step c) is selected from the group consisting of a solid support bearing a pyridinium salt, a cation exchange solid support with an optionally substituted pyridinium, a cation exchange solid support with an optionally substituted imidazolium salt, a solid support bearing an optionally substituted azole selected from the group consisting of imidazole, triazole, tetrazole, a salt of a weak base anion exchange resin with a strong acid, a weak cation exchange resin (carboxylic) in its protonated form, a solid support bearing an optionally substituted phenol, a solid supported carboxylic acid chloride, a solid supported carboxylic acid bromide, a solid supported sulfonic acid chloride, a solid supported sulfonic acid bromide, a solid supported chloroformate, a solid supported bromoformate, a solid supported chlorosulfite, a solid supported bromosulfite, a solid supported phosphorochloridate, a solid supported phosphorbromidate, and a solid support bound carbodiimide.

14. The method of claim 11, wherein the solid supported oxidizing reagent is selected from the group consisting of solid supported periodates, solid supported permanganates, solid supported osmium tetroxides, solid supported dichromates, solid supported hydroperoxides, solid supported substituted alkylamine oxides, solid supported percarboxylic acid, and solid supported persulfonic acid.

15. The method of claim 11, wherein the solid supported oxidizing reagent is a solid supported sulfurization reagent.

16. The method of claim 15, wherein the solid supported sulfurization reagent is selected from the group consisting of a solid supported tetrathionate, a solid supported alkyl or aryl sulfonyl disulfide, a solid supported optionally substituted dibenzoyl tetrasulfide, a solid supported bis(alkyloxythiocarbonyl)tetrasulfide, a solid supported optionally substituted phenylacetyl disulfide, a solid supported N-[(alkyl or aryl)sulfanyl]alkyl or aryl substituted succinimide and a solid supported (2-pyridinyldithio)alkyl or aryl.

17. The method of claim 11, wherein the solid supported capping agent is a solid supported activated acid, a carboxylic acid chloride, a carboxylic acid bromide, an azolide, a substituted azolide, an anhydride, a chloroformate, a phosphorochloridate, a solid supported phosphoramidite, or a solid supported H-phosphonate monoester.

18. The method of claim 11, wherein $R'_3$ is a silyl group and the solid supported deprotection reagent of step e) is a solid-supported ammonium fluoride, or $R'_3$ is levulinic acid; and the solid supported agent of step e) is a solid supported hydrazine or a solid supported hydrazinium.

19. The method of claim 11, wherein $R_3$ of the first compound of step a) is OH.

20. A method comprising reacting an oligonucleotide comprising an internucleotide linkage comprising a P(III) phosphorus atom with a solid supported oxidizing reagent, wherein the solid supported oxidizing reagent is (i) an anion exchange resin complexed with a tetrathionate having the formula $S_4O_6^{-2}$ or (ii) a solid supported cyanoethylthiosulfate having the formula ($NC-CH_2-CH_2-S-SO_3^-$).

* * * * *